United States Patent
Gupta et al.

(10) Patent No.: US 12,211,624 B2
(45) Date of Patent: Jan. 28, 2025

(54) METHODS AND SYSTEMS OF PREDICTING PPE NEEDS

(71) Applicant: Health Solutions Research, Inc., Rockville, MD (US)

(72) Inventors: Ajay Kumar Gupta, Potomac, MD (US); Ramani Peruvemba, McLean, VA (US)

(73) Assignee: Health Solutions Research, Inc., Rockville, MD (US)

( * ) Notice: Subject to any disclaimer, the term of this patent is extended or adjusted under 35 U.S.C. 154(b) by 239 days.

(21) Appl. No.: 17/107,407

(22) Filed: Nov. 30, 2020

(65) Prior Publication Data

US 2021/0166819 A1    Jun. 3, 2021

Related U.S. Application Data

(63) Continuation-in-part of application No. 16/887,608, filed on May 29, 2020, which is a continuation-in-part
(Continued)

(51) Int. Cl.
*G16H 50/30* (2018.01)
*G16H 40/40* (2018.01)
(Continued)

(52) U.S. Cl.
CPC ............. *G16H 50/30* (2018.01); *G16H 40/40* (2018.01); *G16H 50/20* (2018.01); *G16H 50/80* (2018.01)

(58) Field of Classification Search
CPC ........ G16H 50/30; G16H 50/20; G16H 50/80; G16H 40/40
See application file for complete search history.

(56) References Cited

U.S. PATENT DOCUMENTS 6,953,687 B1   10/2005   Rybak et al.
8,758,238 B2    6/2014   Clapp
(Continued)

FOREIGN PATENT DOCUMENTS

CN     113365211 A    9/2021
WO    2016/172614   10/2016
(Continued)

OTHER PUBLICATIONS

Chang et al., "Mobility network models of COVID-19 explain inequities and inform reopening", Nature, vol. 589, 44 pages, Nov. 10, 2020, available at https://www.nature.com/articles/s41586-020-2923-3.
(Continued)

*Primary Examiner* — Stella Higgs
*Assistant Examiner* — Aaisha Abdullah
(74) *Attorney, Agent, or Firm* — HSML P. C.

(57) ABSTRACT

A method of predicting personal protective equipment (PPE) needs is disclosed. The method includes determining a number of PPE users, determining a first burn rate and a second burn rate for a type of PPE, obtaining a number of active patients for a disease and a number of resources, and determining a hospitalization rate for the disease. The method also includes determining a first (and/or a second) PPE rate for the type of PPE based on the number of PPE users, the first (and/or the second) burn rate for the type of PPE, the hospitalization rate for the disease, the number of active patients for the disease, and the number of resources. The method further includes determining an index PPE rate based on a pandemic risk index, the first PPE rate for the type of PPE, the second PPE rate for the type of PPE, and the first burn rate.

20 Claims, 14 Drawing Sheets

Related U.S. Application Data of application No. 16/429,550, filed on Jun. 3, 2019, which is a continuation-in-part of application No. 16/126,537, filed on Sep. 10, 2018, which is a continuation-in-part of application No. 16/024,387, filed on Jun. 29, 2018, now Pat. No. 11,177,040.

(51) Int. Cl.
*G16H 50/20* (2018.01)
*G16H 50/80* (2018.01)

(56) References Cited

U.S. PATENT DOCUMENTS

| | | |
|---|---|---|
| 9,152,918 B1 | 10/2015 | McNair |
| 11,109,194 B1 | 8/2021 | Pinheiro et al. |
| 11,504,011 B1 | 11/2022 | Jain et al. |
| 2002/0183965 A1 | 12/2002 | Gogolak |
| 2005/0131740 A1 | 6/2005 | Massenzio et al. |
| 2005/0203773 A1 | 9/2005 | Soto et al. |
| 2006/0115485 A1 | 6/2006 | Losonsky |
| 2006/0129427 A1 | 6/2006 | Wennberg |
| 2008/0091471 A1 | 4/2008 | Michon et al. |
| 2008/0172262 A1 | 7/2008 | An et al. |
| 2008/0228824 A1 | 9/2008 | Kenedy et al. |
| 2009/0216564 A1 | 8/2009 | Rosenfeld |
| 2011/0225007 A1 | 9/2011 | Theis |
| 2011/0288886 A1 | 11/2011 | Whiddon et al. |
| 2013/0185097 A1 | 7/2013 | Saria et al. |
| 2013/0197942 A1* | 8/2013 | Chiu et al. |
| 2013/0339053 A1 | 12/2013 | Jacobs et al. |
| 2014/0081652 A1 | 3/2014 | Klindworth |
| 2014/0236668 A1 | 8/2014 | Young et al. |
| 2015/0064137 A1 | 3/2015 | Lichtsteiner et al. |
| 2015/0213225 A1 | 7/2015 | Amarasingham et al. |
| 2015/0242586 A1 | 8/2015 | Kagen |
| 2016/0110512 A1 | 4/2016 | Adjaoute |
| 2016/0314256 A1 | 10/2016 | Su et al. |
| 2016/0315723 A1 | 10/2016 | Koriyama et al. |
| 2016/0316723 A1 | 11/2016 | Wall et al. |
| 2016/0378932 A1 | 12/2016 | Sperling et al. |
| 2017/0004275 A1 | 1/2017 | Mehta et al. |
| 2017/0011323 A1* | 1/2017 | Farioli Brioschi ...... G07C 9/28 |
| 2017/0061077 A1 | 3/2017 | Cline et al. |
| 2017/0076058 A1 | 3/2017 | Stong |
| 2017/0103172 A1* | 4/2017 | Fink et al. |
| 2017/0109493 A1 | 4/2017 | Hogg et al. |
| 2017/0132371 A1 | 5/2017 | Amarasingham et al. |
| 2017/0199979 A1 | 7/2017 | Reiner |
| 2017/0286622 A1 | 10/2017 | Cox et al. |
| 2017/0351834 A1 | 12/2017 | Cahan et al. |
| 2018/0012470 A1* | 1/2018 | Kritzler ................ G06Q 50/265 |
| 2018/0137235 A1 | 5/2018 | Meshkin |
| 2018/0330824 A1 | 11/2018 | Athey et al. |
| 2018/0366221 A1* | 12/2018 | Crehore ................ G06F 16/211 |
| 2019/0073618 A1* | 3/2019 | Kanukurthy ........... G08B 21/02 |
| 2019/0088356 A1 | 3/2019 | Oliver et al. |
| 2019/0088373 A1 | 3/2019 | Sarmentero |
| 2019/0133536 A1 | 5/2019 | Roberts et al. |
| 2019/0182749 A1* | 6/2019 | Breaux et al. |
| 2019/0272925 A1 | 9/2019 | Barrett et al. |
| 2020/0225189 A1* | 7/2020 | Verma et al. |
| 2020/0294680 A1 | 9/2020 | Gupta et al. |
| 2020/0349324 A1 | 11/2020 | Ostby et al. |
| 2020/0373018 A1 | 11/2020 | Segal |
| 2021/0043330 A1 | 2/2021 | Ikeshima |
| 2021/0142910 A1 | 5/2021 | Hafez et al. |
| 2021/0166819 A1 | 6/2021 | Gupta et al. |
| 2021/0313075 A1 | 10/2021 | Mc Namara et al. |
| 2021/0319884 A1 | 10/2021 | Day et al. |
| 2021/0366621 A1* | 11/2021 | Miff et al. |
| 2022/0059242 A1* | 2/2022 | Schneider et al. |
| 2022/0369925 A1 | 11/2022 | Lord et al. |
| 2023/0070131 A1* | 3/2023 | Frieder ................ G16H 50/20 |
| 2023/0343460 A1 | 10/2023 | Gnanasambandam et al. |

FOREIGN PATENT DOCUMENTS

| | | |
|---|---|---|
| WO | 2021226853 A1 | 11/2021 |
| WO | 2022074623 A1 | 4/2022 |

OTHER PUBLICATIONS

Chen et al., "Reality mining: A prediction algorithm for disease dynamics based on mobile big data," Information Sciences 379 ( 2017) 82-93 (Year: 2017) ; Cited in Notice of Allowance issued in U.S. Appl. No. 16/024,387.

"Implementation of Mitigation Strategies for Communities with Local COVID-19 Transmission," Department of Health and Human Services USA—CDC Mar. 12, 2020 (Year: 2020).

* cited by examiner

METHODS AND SYSTEMS OF PREDICTING PPE NEEDS

CROSS-REFERENCE TO RELATED APPLICATIONS

This application is a continuation-in-part of U.S. application Ser. No. 16/887,608, filed on May 29, 2020, which is a continuation-in-part of U.S. application Ser. No. 16/429,550, filed on Jun. 3, 2019, which is a continuation-in-part of U.S. application Ser. No. 16/126,537, filed on Sep. 10, 2018, which is a continuation-in-part of U.S. application Ser. No. 16/024,387, filed on Jun. 29, 2018, which claims benefit of provisional application 62/602,661, filed on May 1, 2017, the entire disclosures of which are hereby incorporated by reference herein.

FIELD OF THE DISCLOSURE

The present disclosure is generally related to an advanced smart pandemic and infectious disease response engine; in one or more example embodiments, to predicting a spread of an infectious disease and evaluating pandemic response resources; to predicting risk areas of the infectious disease including areas of high risk of mortality and/or critical cases due to the infection, and to predicting the amount of personal protective equipment (PPE) needs to safely address the specific healthcare issue and/or to facilitate procurement, acquisition, and/or distribution of the PPE.

BACKGROUND

A pandemic is an epidemic of infectious disease occurring on a scale that crosses international boundaries, affecting a substantial number of people. Throughout history, there have been a number of pandemics, including COVID-19 (2019). Strategies for controlling the scope of a pandemic include containment, mitigation, and suppression.

Containment is typically undertaken in the early stages of a pandemic, and may include contact tracing and isolating infected individuals to stop the disease from spreading to the rest of the population. During the containment stage, public health intervention for facilitating infection control and therapeutic countermeasures, such as vaccinations, may be applicable. When it is not possible to contain the spread of the disease, strategic mitigation may be implemented, in which measures are taken to slow the spread of the disease and mitigate its effects on society, including the healthcare system. Containment and mitigation measures may be undertaken simultaneously. Suppression requires more extreme long-term interventions so as to reverse the pandemic by reducing the basic reproduction number to less than one. The suppression strategy, which includes stringent population-wide social distancing, home isolation of cases, and household quarantine, carries with it considerable social and economic costs.

As history shows, a novel virus may lead to, either progressively or simultaneously, international travel restrictions, the cancelation of numerous public events across the globe, and the quarantine and social isolation of millions and potentially billions of people in numerous countries.

SUMMARY

Pandemic response resources are implemented to contain, mitigate, and/or suppress a pandemic. The pandemic response resources include PPE that is critical to ensuring the health, well-being, and viability of personnel such as essential workers including healthcare workers, law enforcement personnel, etc., and/or the general public. PPE may include non-surgical masks, surgical masks, gowns, gloves, etc. The COVID-19 pandemic, beginning in 2019, exposed how a globally connected healthcare supply chain system may at times be unable to meet needs in the event of a global emergency. The shortage of PPE experienced even in industrialized nations increased the risk of contracting and transmitting the pathogens (such as COVID-19 virus) for healthcare and essential workers, as well as the patients and the public they serve. Prevention of the PPE shortages, as well as the consequences of such shortages, requires the acquisition and distribution of PPE in advance of a pandemic, and requires predicting PPE needs for health systems, organizations, government entities, etc. at the national, state, county, and local levels, to protect the essential workforces and the public they serve upon the actual occurrence of a pandemic. It will be appreciated that addressing PPE needs and/or shortages further requires analysis of actual PPE needs so that health systems and other users may work with suppliers, distributors, and/or manufacturers to ensure minimum required PPE levels are met.

Embodiments disclosed herein may address PPE needs by establishing an analytical method, program, tools, and systems to estimate PPE needs in advance of, during, and/or throughout a pandemic lifecycle. Embodiments disclosed herein may help to guide individual health systems to determine quantities of PPE that may be sufficient to meet their needs, to guide government entities at multiple levels to plan for emergency stockpiles, and/or to guide PPE suppliers and manufacturers in planning for the production and distribution of PPE necessary to meet demand related to the current as well as a potential future pandemic or similar health emergency. Embodiments disclosed herein may not only ensure sufficient availability of PPE when, where, and to whom needed, but also may help to avoid buyers from acquiring excess PPE, which may become a financial burden and cause PPE shortages for others.

In at least one example embodiment, a method of predicting a spread of an infectious disease and evaluating pandemic response resources includes generating a predictive model, obtaining a set of patient data and a set of resource data (e.g., the location, quantity, and/or availability of doctors, nurses, beds, test kits, ventilators, PPE, MRI machines, critical medications, and/or other essential medical equipment and/or devices etc.) from a plurality of data sources, geocoding the patient and resource data, loading the data into a geospatial data analytic application (or spatial data infrastructure), and applying the predictive model to the set of patient data and the set of resource data. The method also includes determining resource levels based on an output of the predictive model, outputting the resource levels formatted for integration into an electronic health records system (and/or supply chain management platforms, inventory management platforms, etc.) to trigger a resource allocation and/or procurement, and adjusting the set of resource data based on the resource allocation and/or procurement.

It will be appreciated that the output (including health pandemic risk indices, resource levels, etc.) of the predictive model may also be integrated into a data processing system including software systems supporting disaster and emergency response platforms, such as an electronic health records system, other clinical application, emergency response management system, supply chain tracking and management software system, or any other suitable data processing system, to inform users such as logistics firms, manufacturers, and/or distributors the areas of heightened need for medical equipment and/or supplies so that the users may have distinct advantages (e.g., knowledge of scarcity of particular products in particular areas, etc.) in selling their products into those areas/markets. This may provide information on what the needed supplies are/will be, so that those needs may be met.

In at least another example embodiment, a method of predicting risk areas of an infectious disease includes generating a predictive model, and obtaining a set of patient data and a set of condition data from a plurality of data sources. The set of patient data may be obtained from patients having either a first (e.g., primary) identified risk or a second (e.g., secondary) identified risk. The method also includes applying the predictive model to the set of patient data and the set of condition data, determining mitigations for the patients having the first identified risk and patients having the second identified risk based on an output of the predictive model, and outputting the mitigations formatted for integration into an electronic health records system.

In at least yet another example embodiment, a method of predicting PPE needs in the event of a pandemic or other wide-spread health emergency includes determining a number of PPE users, determining a first burn rate and a second burn rate for a type of PPE, obtaining a number of currently diagnosed patients for a disease or virus, and a number of resources, and determining a hospitalization rate for patients diagnosed with the disease or virus. As defined herein, the term "burn Rate" may refer to a daily rate of utilization of PPE equipment, by type, and by an individual user. The method also includes determining a first (and/or a second) PPE rate for the type of PPE based on the number of PPE users, the first (and/or the second) burn rate for the type of PPE, the hospitalization rate for the disease or virus, the number of currently diagnosed patients with the disease or virus, and/or the number of resources (hospital beds, etc.) required for treating the hospitalized patients, etc. The method further includes determining an index PPE rate based on a pandemic risk index, the first PPE rate for the type of PPE, the second PPE rate for the type of PPE, and the first burn rate.

In at least one example embodiment, a non-transitory computer-readable medium has computer-readable instructions that, if executed by a computing device, cause the computing device to perform operations including the above methods and/or other methods disclosed herein.

It will be appreciated that the above embodiments are merely illustrative of the technical concept and features of the pandemic and infectious disease response engine, and these embodiments are to provide a person skilled in the art with an understanding of the contents of the response engine in order to implement the response engine without limiting the scope of protection of the response engine. Any features described in one embodiment may be combined with or incorporated/used into the other embodiment, and vice versa. The equivalent change or modification according to the substance of the response engine should be covered by the scope of protection of the response engine.

It will be appreciated that the response engine disclosed herein may provide a predictive tracking and modelling tool for the spread of infectious disease. By leveraging the geospatial tracking capabilities, artificial intelligence based predictive analytics, and health and social data sets, the response engine may track the disease flow and identify at-risk areas for potential future spread of contagion. The modelling may follow a phased approach (e.g., local, regional, national, and international) that expands both the geographic region and improves accuracy of the prediction in each successive phase. The response engine may allow health systems and health authorities to deploy limited resources ahead of the movement of disease, as opposed to reactive measures that at times prove to be insufficient in halting the spread of the contagion or in treating the infected. It will also be appreciated that the output of the response engine (e.g., health pandemic risk indices, etc.) may be integrated into software systems supporting disaster and emergency response management platforms. The health pandemic risk indices include the Transmission Risk Index (TRI) and the Mortality Risk Index and may be integrated into, for example, a data processing system such as an electronic health records system, other clinical application, emergency response management system, supply chain management system, or any other suitable data processing system, including Federal Emergency Management Agency (FEMA)'s emergency response management platform allowing FEMA, as the response coordinating body, to deploy medical and other resources to potential high risk areas in advance high rates of infection. The disaster and emergency response management platforms may be at the global and/or national level, as well as at the State, county, and/or local levels.

It will also be appreciated that the response engine disclosed herein may provide data crucial for pandemic risk management and real-time capacity planning to thereby facilitate a pandemic response. Pandemic response planning and execution require knowledge of available resources, such as the locations and/or availability of medical facilities (including other existing facilities that can be converted into medical facilities in an emergency/pandemic scenario) and equipment; as well as an understanding of the risk of potential supply chain disruptions and dependencies, such as components of key medications and essential resources, in real time. The response engine facilitates identification of pandemic response resources and tracking of global supply chains. The response engine may identify and track the flow of risks to global supply chains and, utilizing such information, provide a robust platform for pandemic management. The response engine may further facilitate monitoring pandemic-related supply chain disruptions across all sectors of an economy.

It will further be appreciated that the response engine disclosed herein may assist and facilitate quarantine/self-quarantine efforts. The response engine may leverage identified high risk geographic areas, as well as assess environmental factors that may potentially exacerbate or inhibit the spread of the pandemic, such as the incubation temperature, humidity, and other environmental factors for viral replication. The response engine may produce recommendations for which areas of a community should be considered for quarantine and/or decontamination, as well as areas of a community in which social isolation should be implemented.

The response engine may contribute to reduction of mental health issues related to social isolation (e.g., cabin fever), by using e.g., data from remote sensors. For example, the response engine may receive, and store, information from personal medical devices and wearable sensors to facilitate monitoring of the mental and emotional well-being of individuals subject to social distancing and quarantining.

By accurately assessing when and where the environment is least conducive to the growth and spread of the pathogen, determinations as to when and where resumption of social interaction constitutes an acceptable risk, prudent decisions may be made as to when mobility levels and the associated economic activity may return to normal levels. Accordingly, the response engine may facilitate upward and downward scaling of the quarantine/de-quarantine efforts as the number of people under quarantine expands and eventually contracts.

The response engine may further facilitate generating quarantine plans to monitor and guide those under social isolation and/or quarantine, as well as plans to de-quarantine impacted communities in a structured and orderly manner. That is, the response engine may facilitate the management of large-scale social isolation by balancing the risk of contagion against the risk of adverse mental health consequences for individuals and economic loss by communities at-large. For example, the response engine may facilitate generating an action plan to use drones to deliver needed supplies to the elderly and others who are in quarantine or social isolation in a particular community. Then, as the quarantine is lifted or eased, the response engine may facilitate generating an orderly quarantine release plan. The response engine may be leveraged in future pandemic situations and in other cities and regions to guide quarantine response. It will be appreciated that the response engine can support decision making in multiple parts of the world simultaneously.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

The present disclosure provides a detailed and specific description that refers to the accompanying drawings. The drawings and specific descriptions of the drawings, as well as any specific or alternative embodiments discussed, are intended to be read in conjunction with the entirety of this disclosure. The pandemic and infectious/contagious disease response engine may, however, be embodied in many different forms and should not be construed as being limited to the embodiments set forth herein; rather, these embodiments are provided by way of illustration only and so that this disclosure will be thorough, complete and fully convey understanding to those skilled in the art.

References are made to the accompanying drawings that form a part of this disclosure and which illustrate embodiments in which the systems and methods described in this specification may be practiced.

Figure 1:
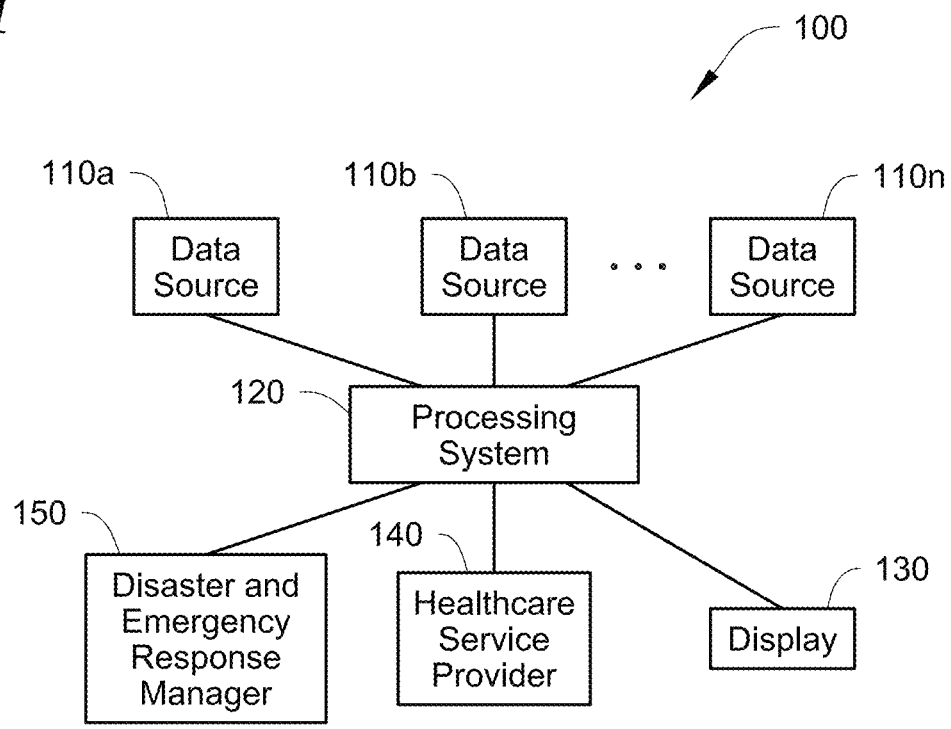

FIG. 1 is a schematic diagram of an advanced smart pandemic and infectious disease response engine, according to at least one example embodiment described herein.

Figure 2:
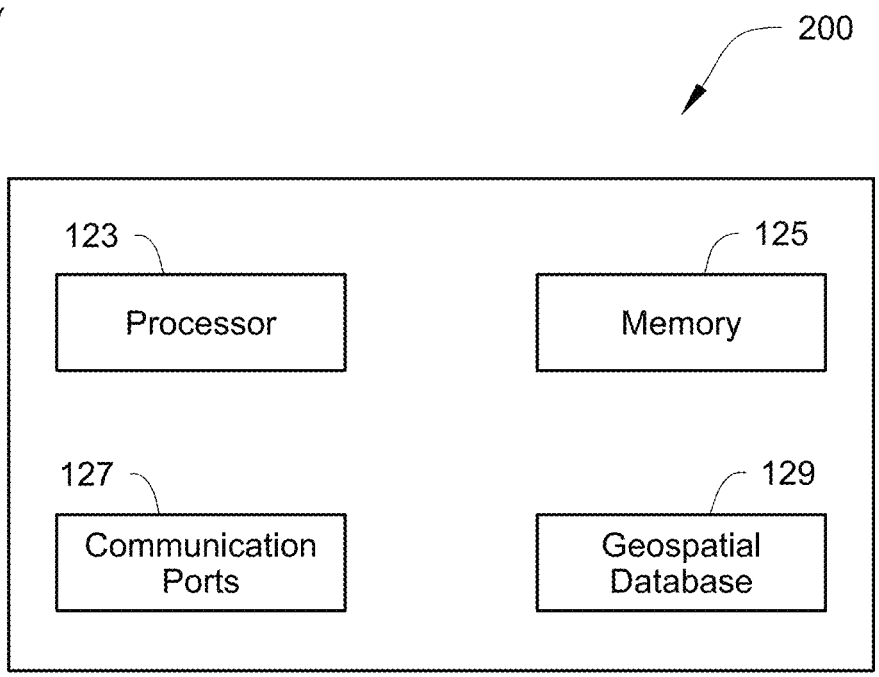

FIG. 2 is a schematic diagram of a processing system, according to at least one example embodiment described herein.

Figure 3:
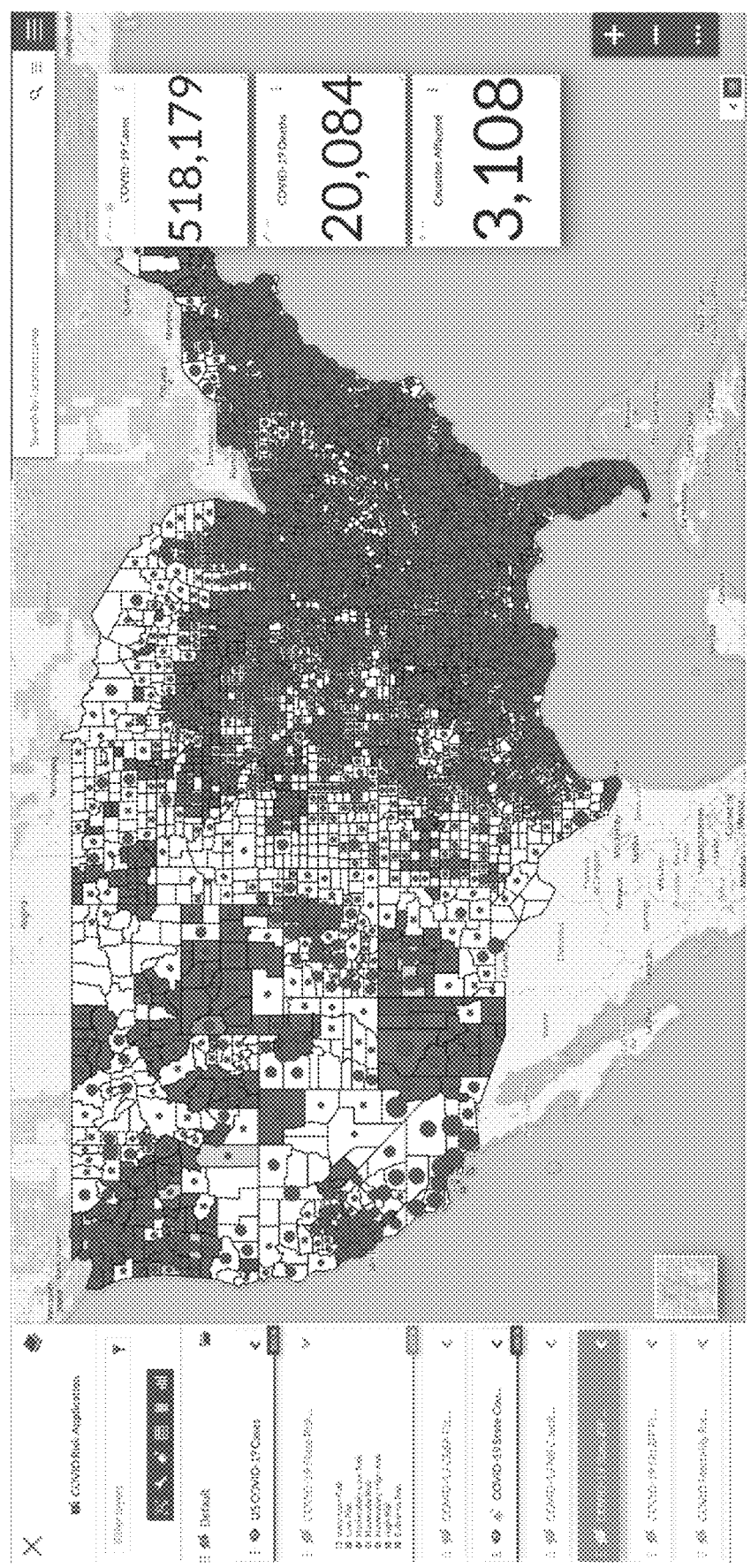

FIG. 3 shows an example map generated by an advanced smart pandemic and infectious disease response engine, according to at least one example embodiment described herein.

Figure 4:
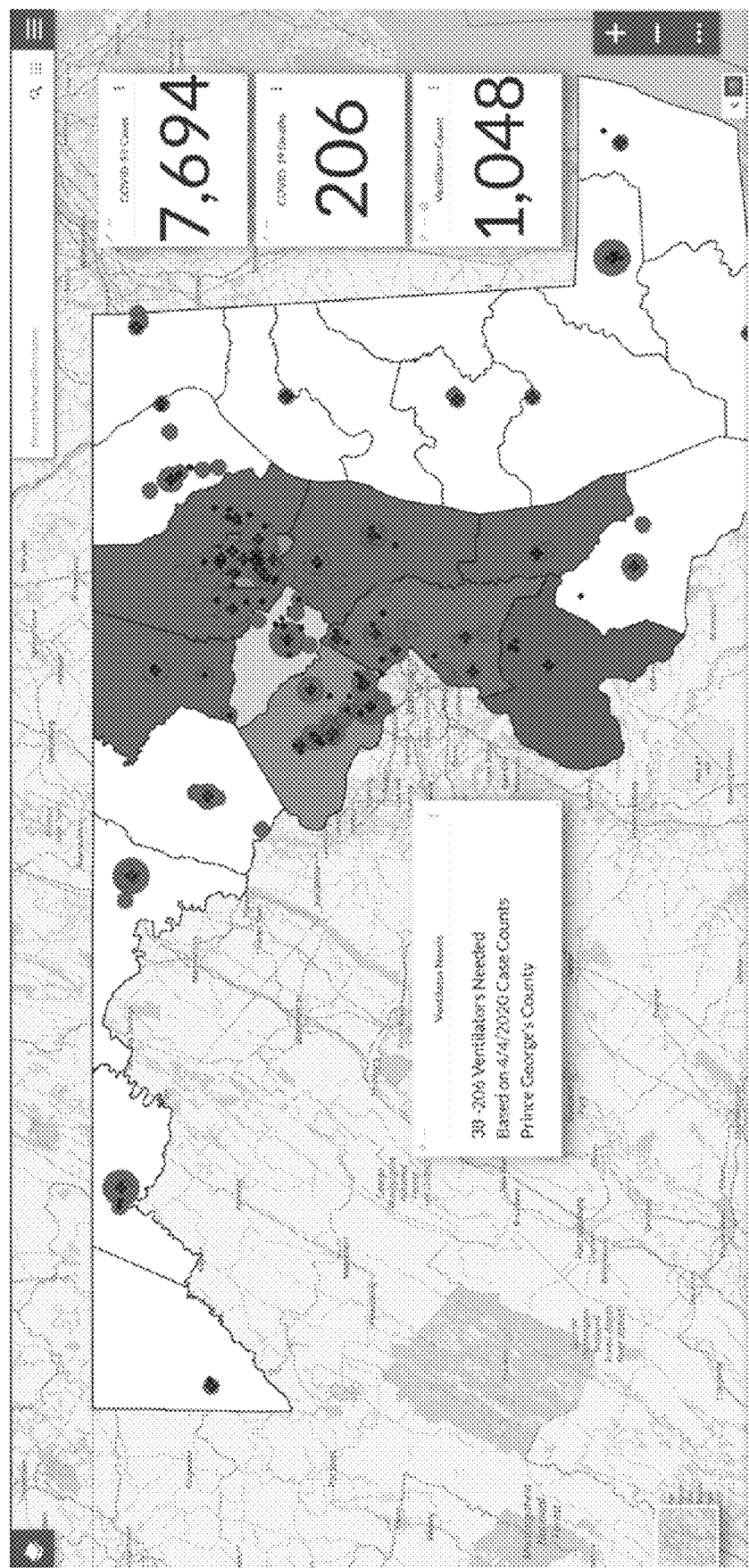

FIG. 4 shows another example map generated by an advanced smart pandemic and infectious disease response engine, according to at least one example embodiment described herein.

Figure 5:
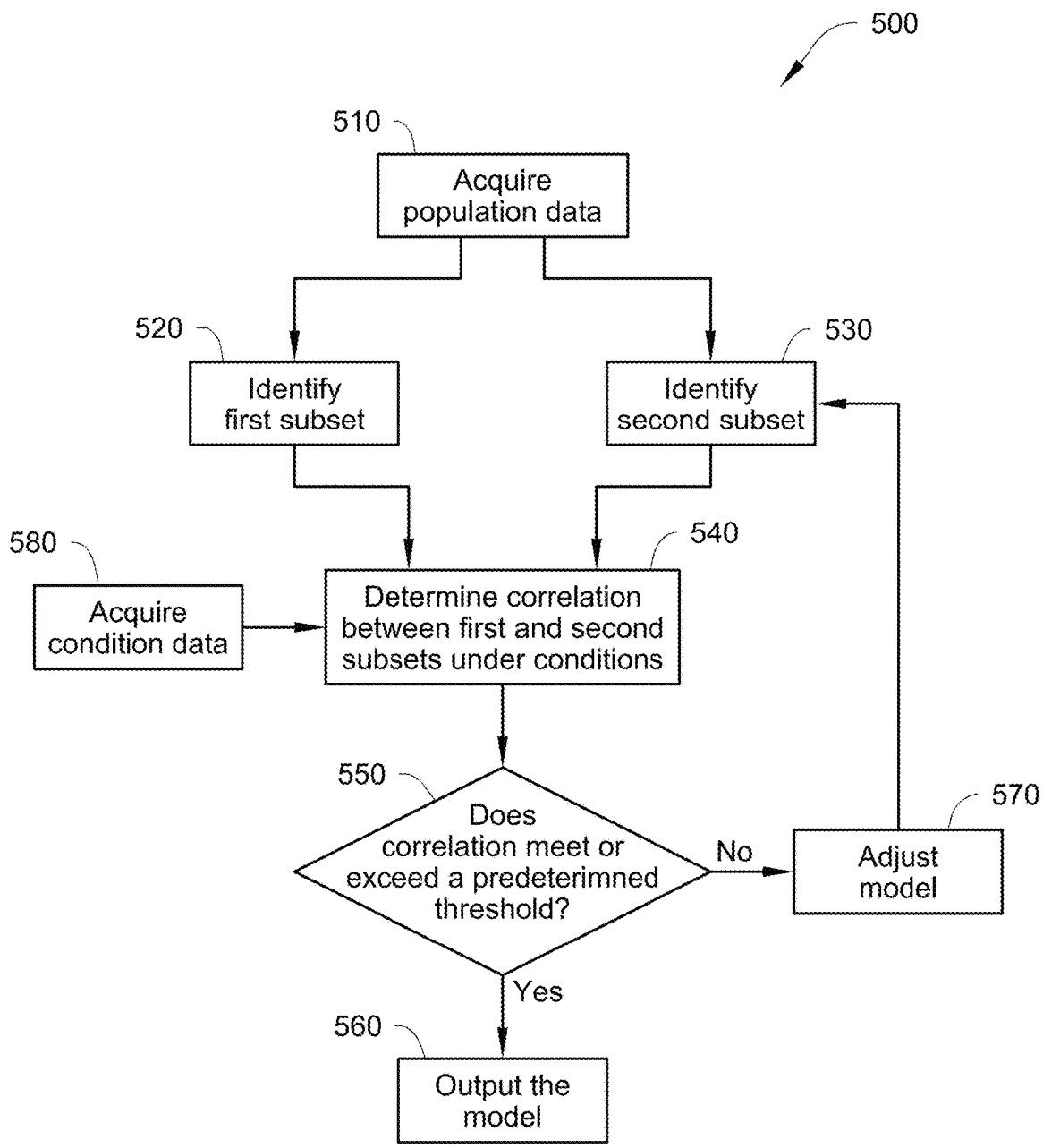

FIG. 5 shows an example processing flow for a response engine to generate a pandemic predictive model, according to at least one example embodiment described herein.

Figure 6:
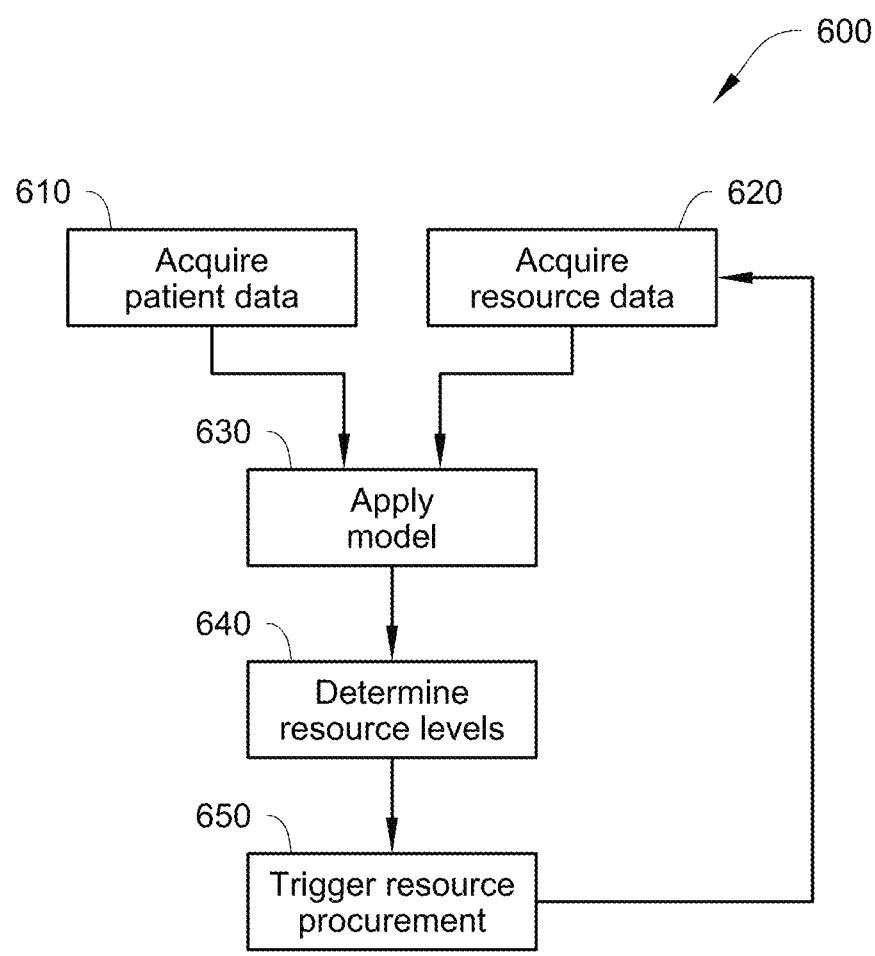

FIG. 6 shows an example processing flow for a response engine to track resource levels, according to at least one example embodiment described herein.

Figure 7:
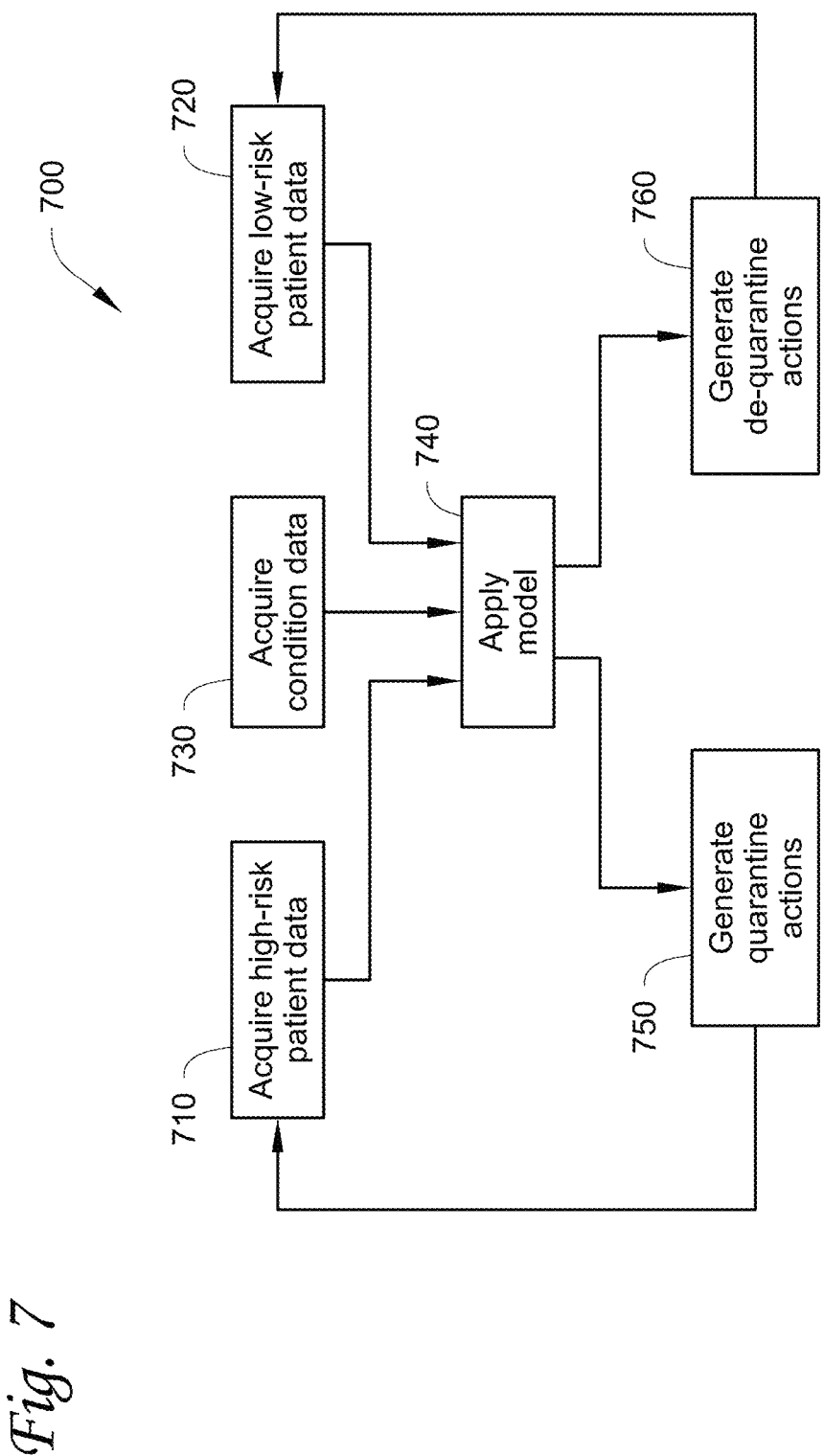

FIG. 7 shows an example processing flow for a response engine to facilitate generating quarantine and/or de-quarantine plans, according to at least one example embodiment described herein.

Figure 8:
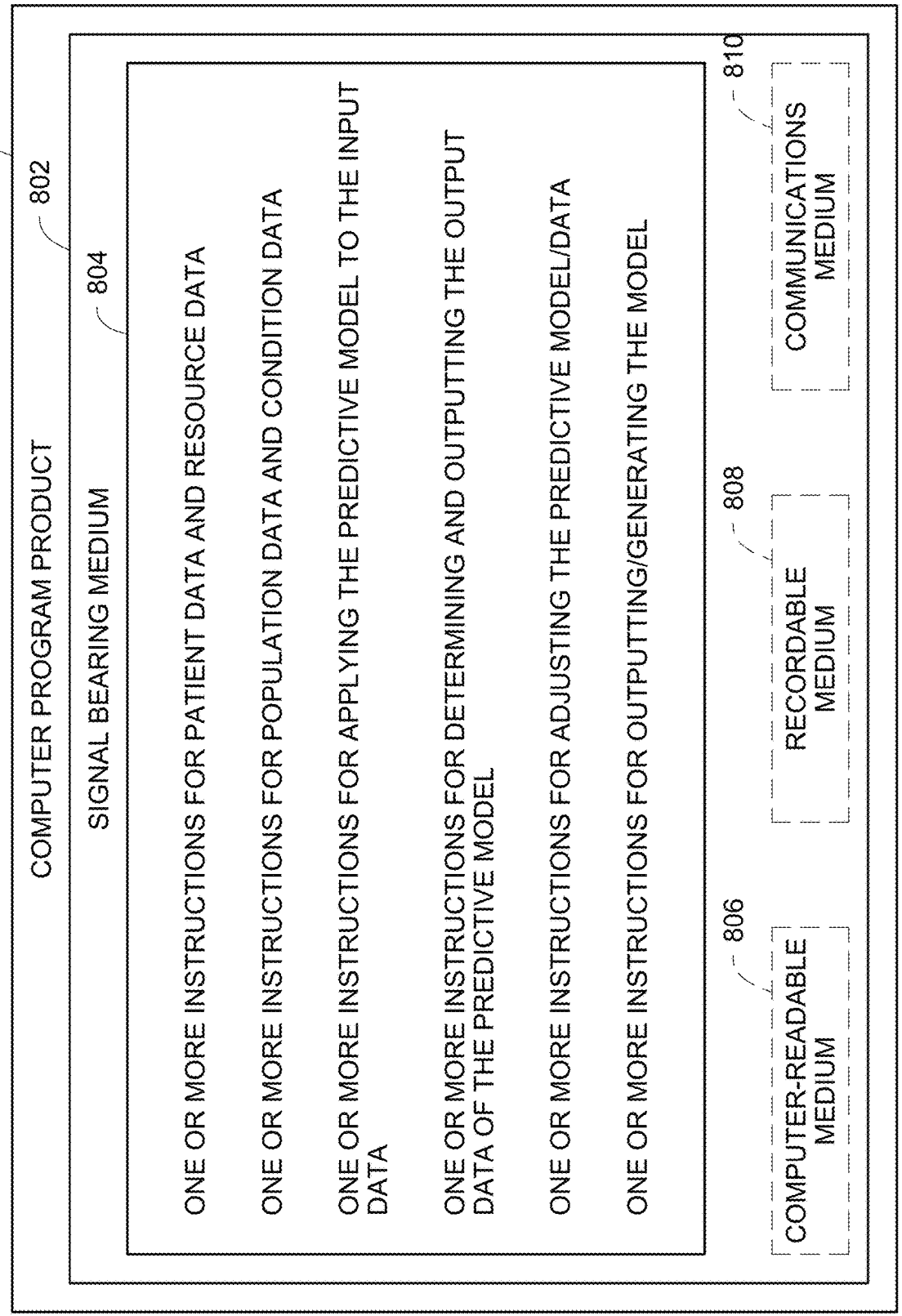

FIG. 8 illustrates at least one computer program product that may be utilized to provide an advanced smart pandemic and infectious disease response engine, according to at least one example embodiment described herein.

Figure 9:
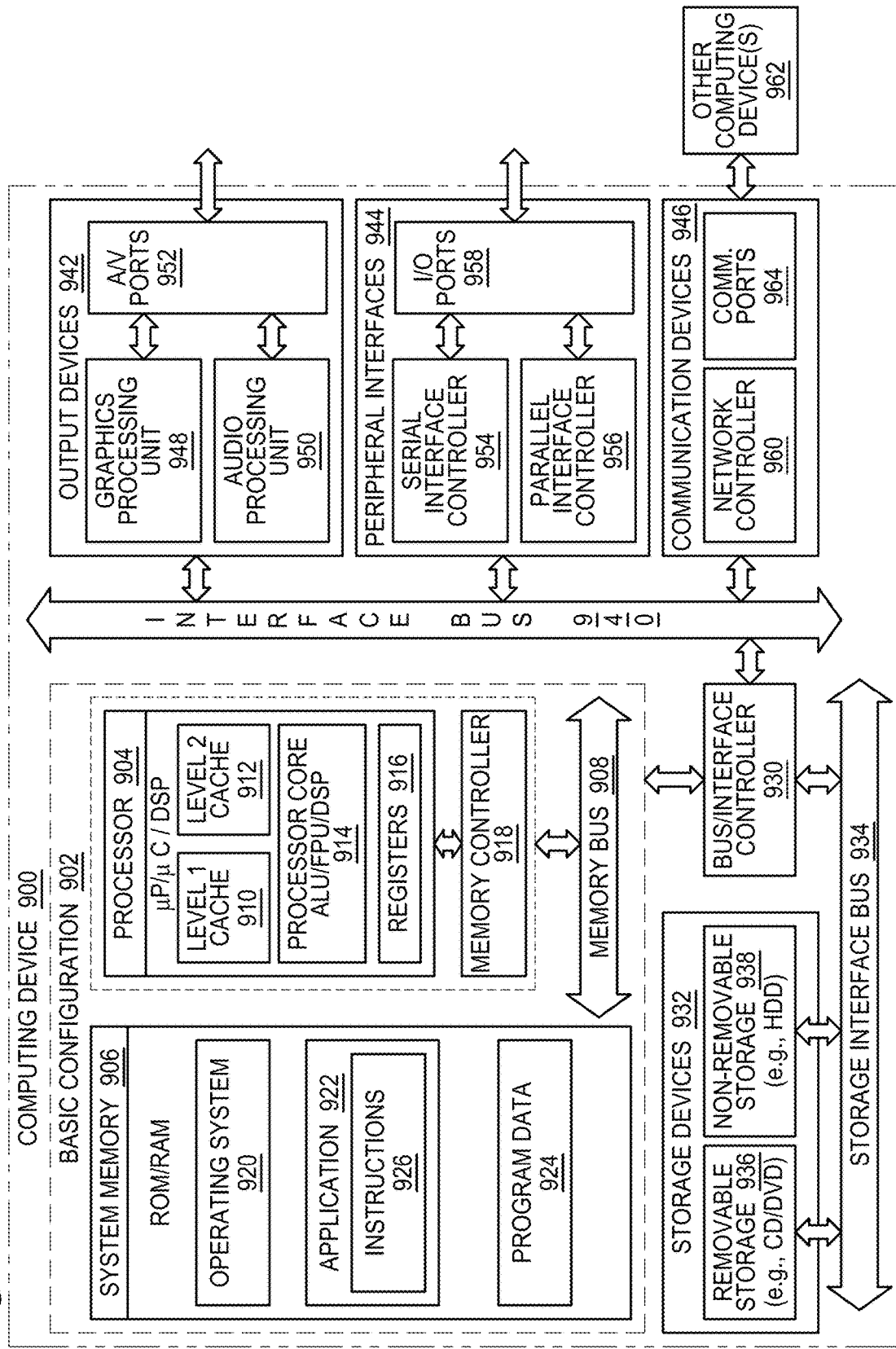

FIG. 9 shows a block diagram illustrating an example computing device by which various example solutions described herein may be implemented, according to at least one example embodiment described herein.

Figure 10:
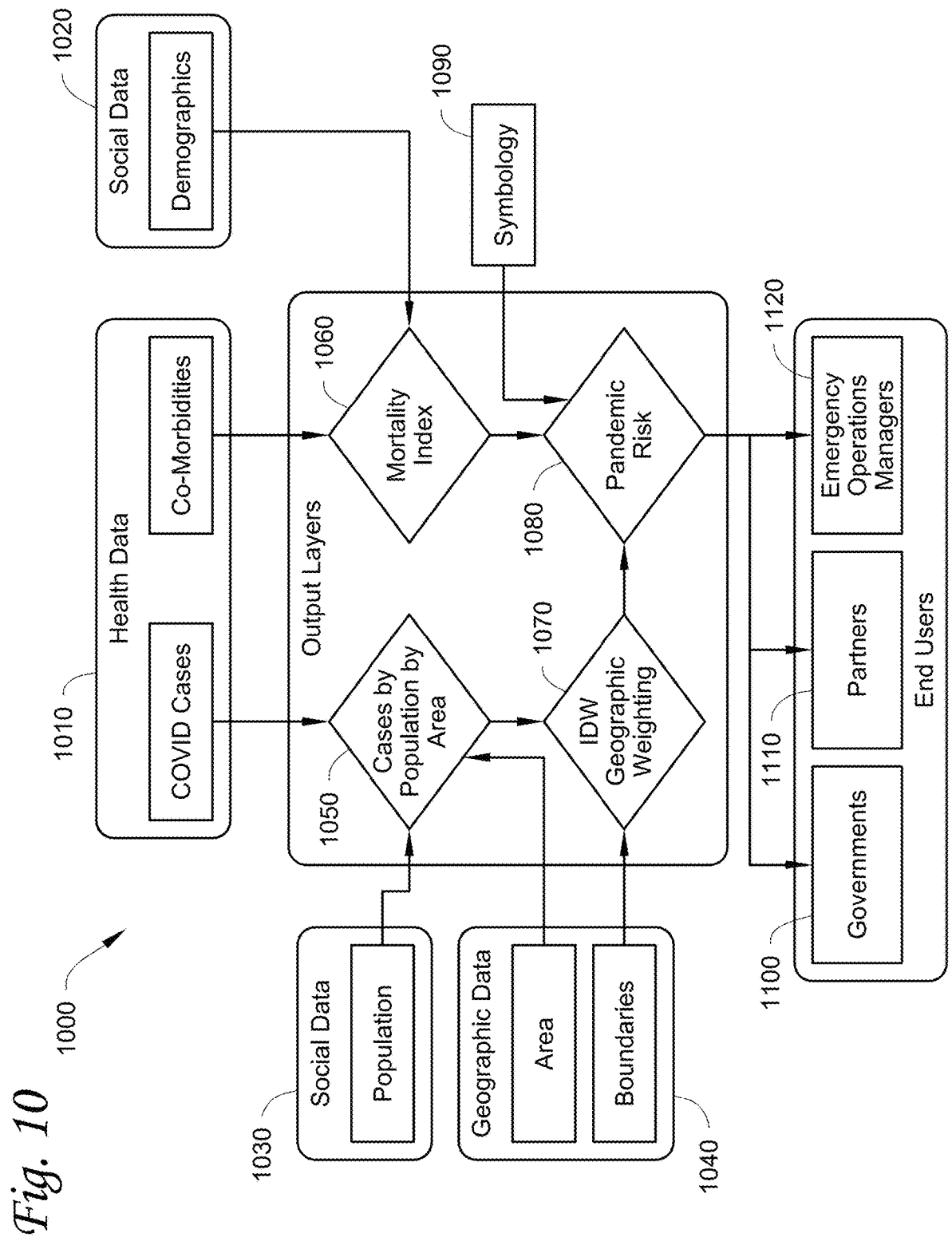

FIG. 10 illustrates a work flow of an advanced smart pandemic and infectious disease response engine, according to at least one example embodiment described herein.

Figure 11:
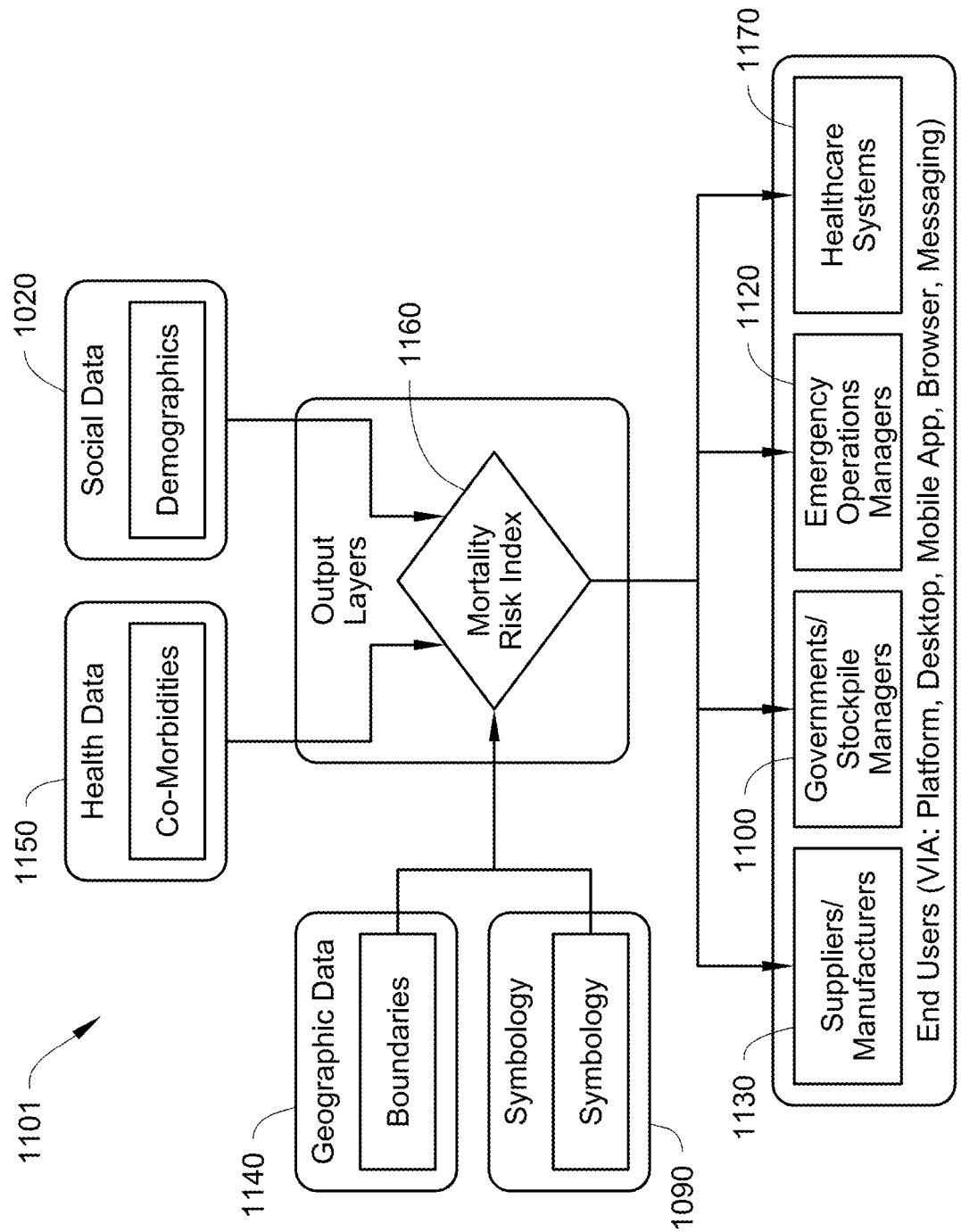

FIG. 11 illustrates a work flow of predicting a Mortality Risk Index, according to at least one example embodiment described herein.

Figure 12:
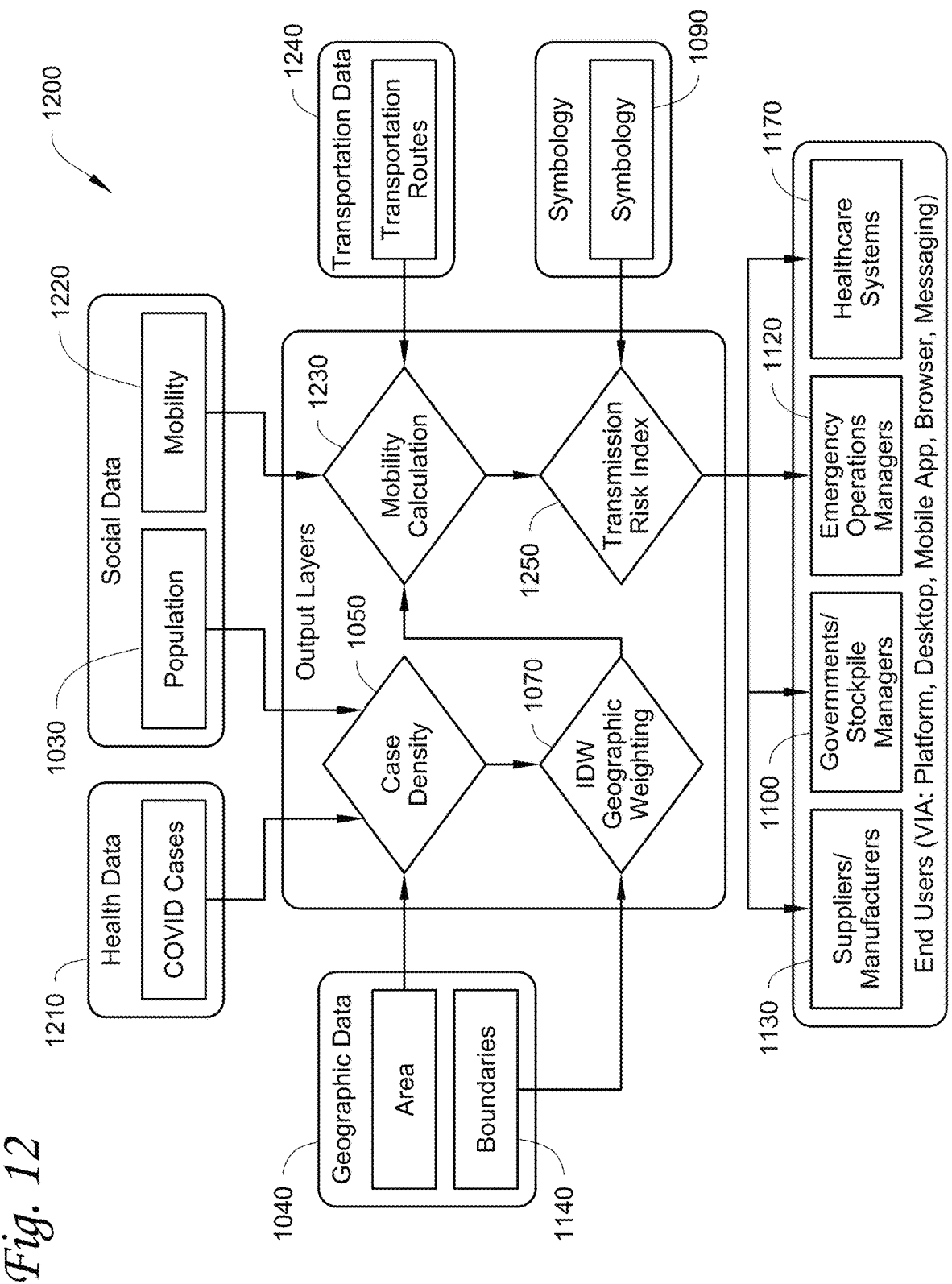

FIG. 12 illustrates a work flow of predicting a Transmission Risk Index, according to at least one example embodiment described herein.

Figure 13:
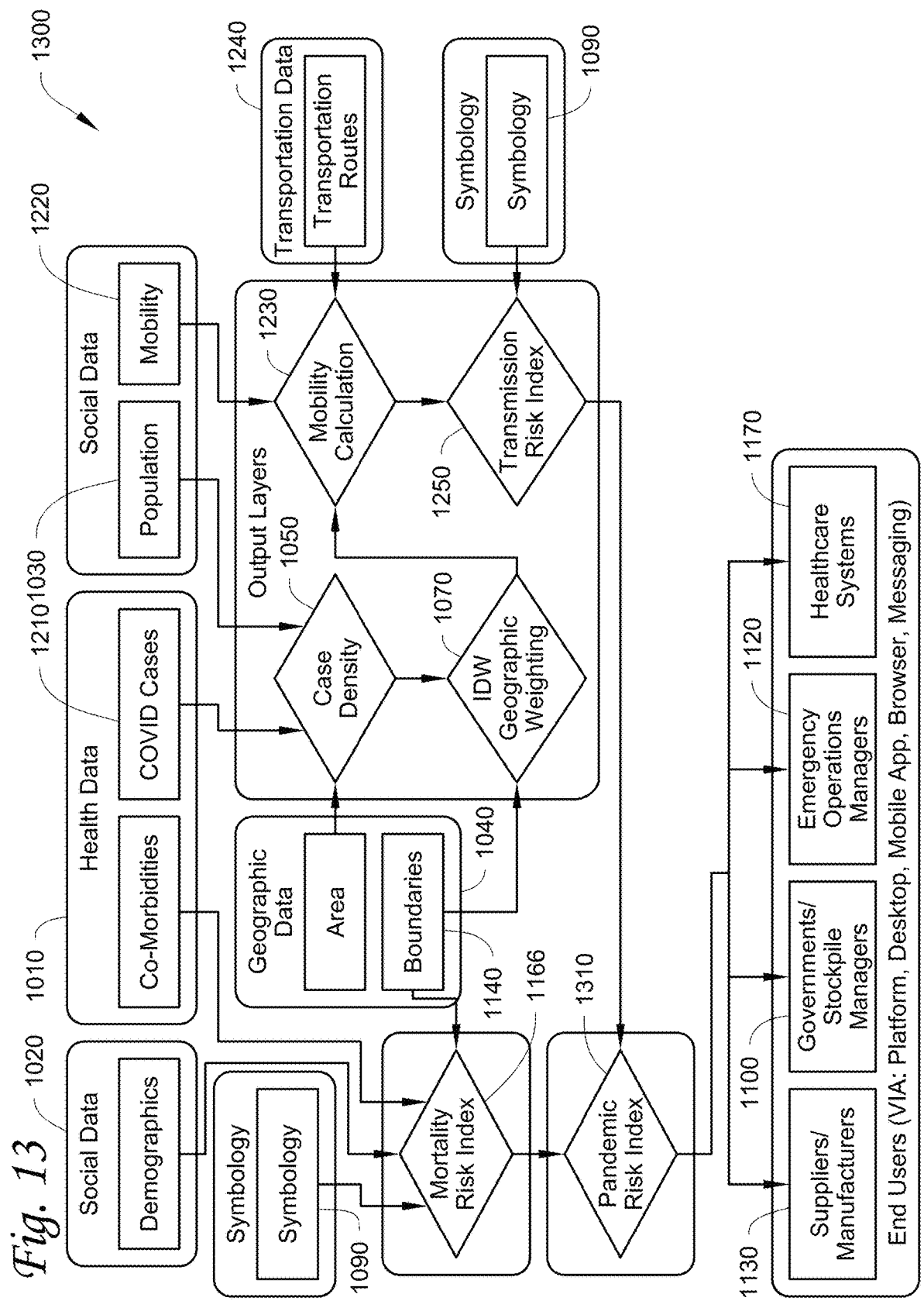

FIG. 13 illustrates a work flow of predicting a Pandemic Risk Index, according to at least one example embodiment described herein.

Figure 14:
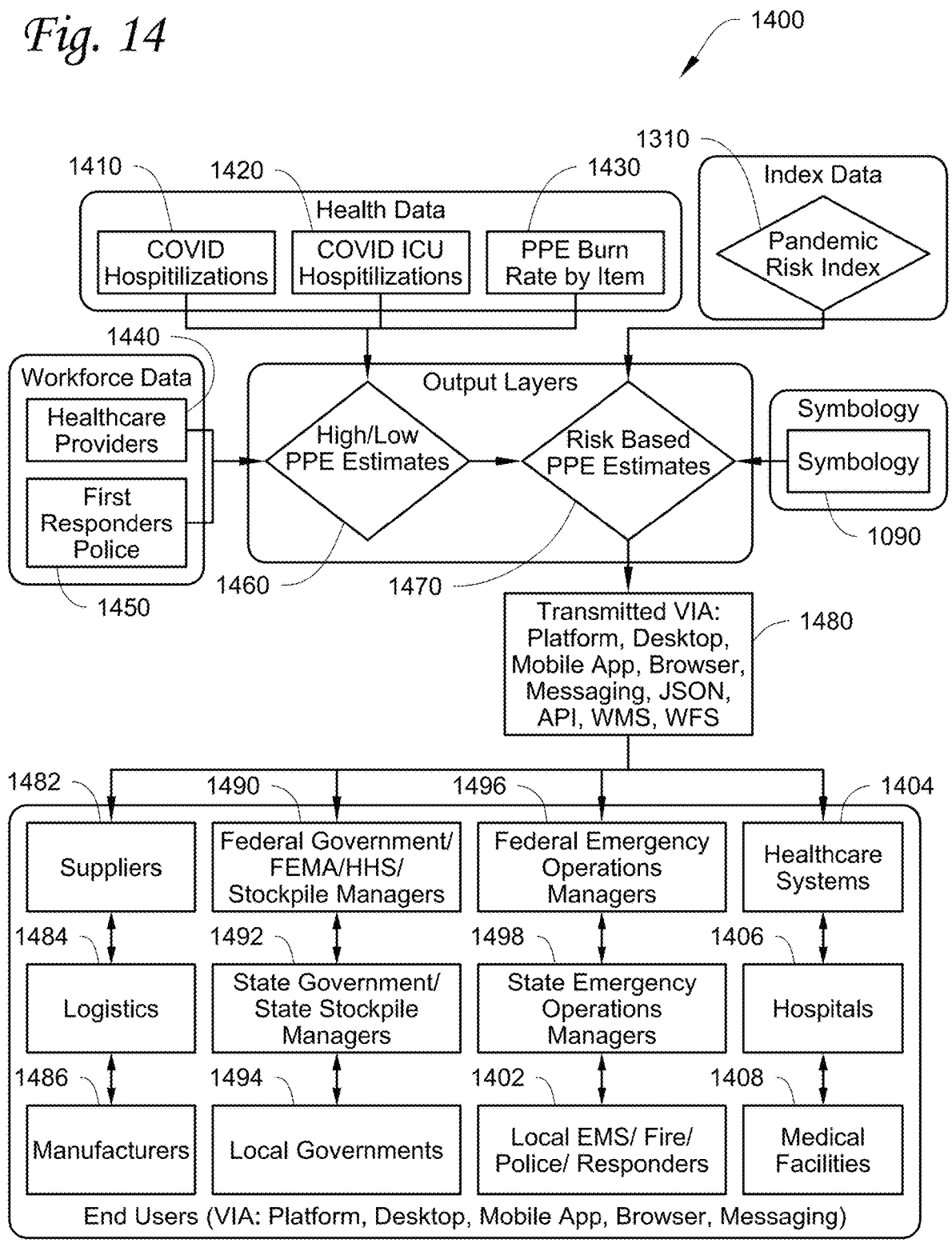

FIG. 14 illustrates a work flow of predicting PPE needs, according to at least one example embodiment described herein.

Figure 15:
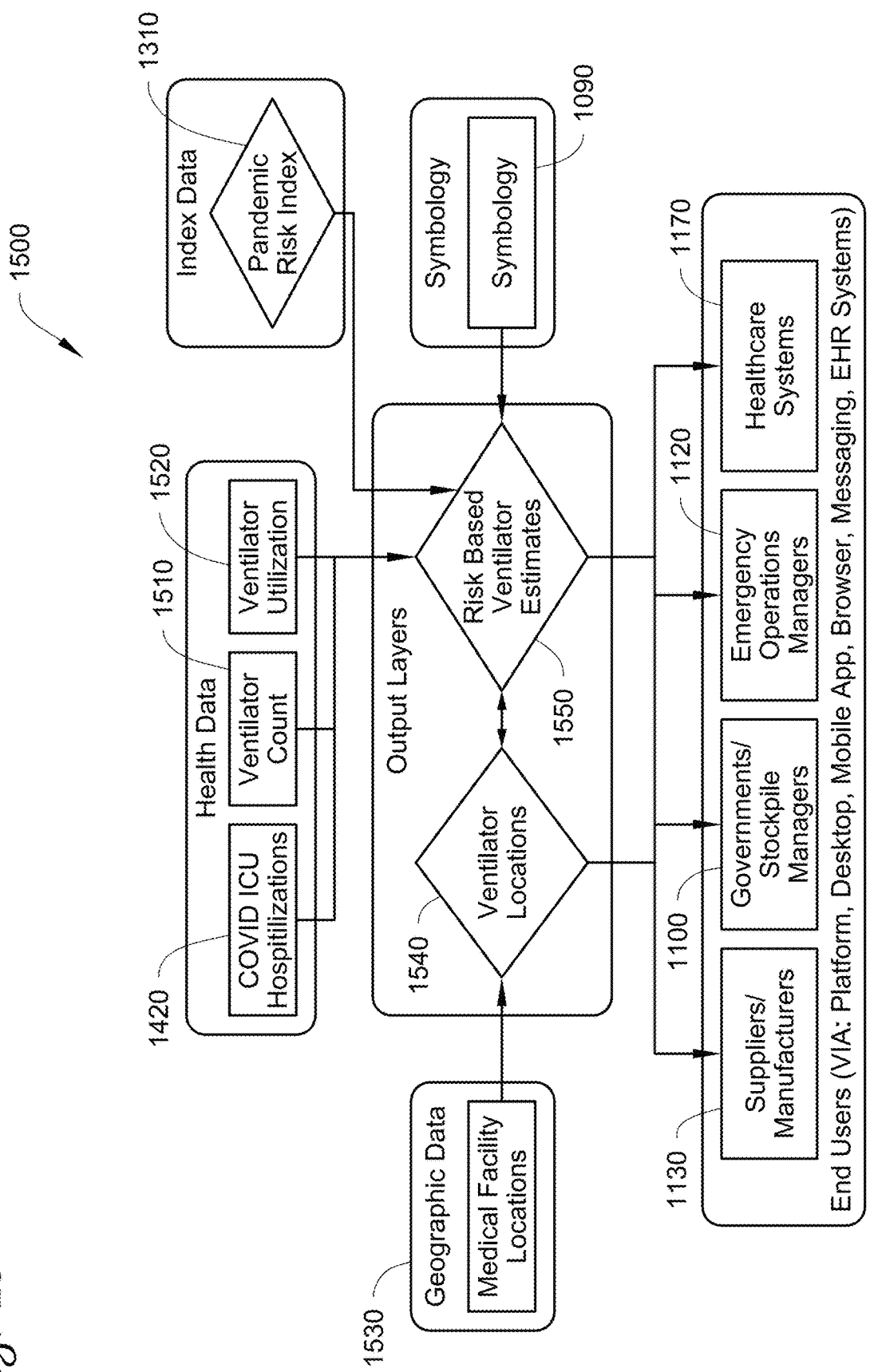

FIG. 15 illustrates a work flow of predicting ventilator needs, according to at least one example embodiment described herein.

DETAILED DESCRIPTION

Some embodiments of this disclosure, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a", "an" and "the" include plural references unless the context clearly dictates otherwise. Although any systems and methods similar or equivalent to those described herein may be used in the practice or testing of embodiments of the present disclosure, the preferred, systems and methods are now described.

It will be appreciated that "risk area" or "risk zone" may refer to geographical area(s) where people may be at risk of being affected by (e.g., exposed to and/or potentially infected by) the infectious disease to varying degrees and/or varying levels of viral load. As defined herein, the terms "high risk area" and/or "hot zone" may refer to a risk area or a risk zone where the number of people that may be at risk of being affected by the infectious disease relative to the population of the area is greater than a predetermined number (e.g., 5% within a city/town, a county, a State, etc.). As defined herein, the terms "low risk area" and/or "low risk zone" may refer to a risk area or a risk zone where the number of people that may be at risk of being affected by the infectious disease relative to the population of the area is equal to or lower than a predetermined number (e.g., 5% within a city/town, a county, a State, etc.). The high/low risk area/zone may also refer to an area that has a high/low risk score/index of transmission of the disease or risk score/index of mortality or critical cases due to the disease. It will be appreciated that the Transmission Risk Index and the Mortality Risk Index may have different risk scores as they are separate risk indices. The scores/indices may be quantified (e.g., 1-5, 1-100, etc., with the higher the scores/indices indicating areas of higher risk). For example, when the risk score is 3 or more over 5 (if the maximum score is 5) (or 60 or more over 100 (if the maximum score is 100)) for an area, the area is a high risk area (hot zone); when the risk score is less than 3 over 5 (or less than 60 over 100) for an area, the area is a low risk area/zone. It will also be appreciated that the risk score may be evaluated in a relative fashion. For example, a risk score for an area (e.g., Area 1) being at or about 20 out of at or about 100 may be considered at a low risk. However, if the surrounding areas have risk scores that are e.g., between 8 and 12 out of 100, then Area 1 may be considered as an area of relatively high risk.

Embodiments of the present disclosure will be described more fully hereafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

FIG. 1 is a schematic diagram of an advanced smart pandemic and infectious disease response engine 100, according to at least one example embodiment described herein. The response engine 100 may be used for pandemic tracking, management, and response, such as predicting a spread of an infectious disease and evaluating pandemic response resources, identifying resources required to adequately and effectively respond to the pandemic, and/or predicting risk areas of the infectious disease. FIG. 1 shows a plurality of data sources 110 a, 110 b, . . . 110 n (collectively, "data sources 110" hereafter), which may be communicatively coupled to a processing system 120. Processing system 120 may be communicatively coupled to at least one of a display 130, a healthcare service provider 140 (e.g., a hospital, other point-of-care provider, or a governmental health department, etc.), and disaster and emergency response managers (e.g., FEMA, etc.). By way of example and without limitation, one or more of the communicative couplings may be wired or wireless connections as would be understood by one of ordinary skill in the art.

Data sources 110 a, 110 b, . . . 110 n may refer to, but not be limited to, e.g., state health departments and national level health repositories (such as US state health departments and national level health repositories, health repositories for other nations, etc.), America's Health Rankings, County Health Rankings, CDC Wonder, World Health Organization (WHO), The United Nations, Kaiser Family Foundation, other non-profits, educational and research institutions, etc. Data sources may also from businesses data repositories such as airline data (flights, passenger traffic, etc.), cell phone data, and/or any other suitable data sources. Further, not only are the systems described, recited, and foreseen herein not limited to the data sources listed above, but they are not limited in quantity to those shown in FIG. 1. Further still, unless context otherwise requires, the description and recitation henceforth may refer to the singular "data source 110" without being limiting.

The data received from one or more instances of data sources 110 may include, but not be limited to vital health statistics and social determinants of health resources that are available on municipality-levels, e.g., national level, state level, counties, cities, towns, ZIP codes, Census tracts, and Census blocks. As discussed below, the collection of statistical reports for pandemic and infectious disease response, behaviour, and demographic data may be utilized to implement the response engine.

To establish a response to a pandemic and/or infectious disease, examples of information provided by data sources 110 may include various socio-environmental and biological risk factors for those in position to provide assistance, such as, e.g., healthcare service provider 140. Those risk factors may include, but not be limited to: environmental and/or climate changes, population demographics, education and/or racial disparities that may contribute to access to quality health services; socio-economic variables such as social class, income, access to insurance, housing, etc.

Data sources 110 may provide, for example, information relating to one or more of geography, demographics, local transportation, finances (both macro- and micro-), health care availability, law enforcement resources, social media of individuals, socioeconomic statistics, and/or historical health data, which may be cross-referenced as well as correlated to population data, individual patient data, health resource data, and/or health-related condition data. In the context of a pandemic and/or infectious disease response, examples of such information that data sources 110 may provide may include, but are not limited to, patient data (e.g., age, whether a patient is chronically ill or has underlying health condition, whether a patient has been infected by the infectious disease, whether the patient is undergoing treatment for the infectious disease, whether the patient has developed an antibody for the infectious disease, etc.); from EHR (electronic health records) systems, social determinants (e.g., for individuals as well as for a community, financial information, education, travel history, habitat, e.g., long-term care facility or private residency, and fatalities, which, for example, may be obtained from the Centers for Disease Control and prevention and/or local health department. These and other data may be obtained from a variety of private and or government sources.

The response engine 100 may analyse geocoded health, social, and environmental data to identify health risks, as well as determine potential solutions for managing a pandemic on various scales. Data sets (including patients, resources such as availability of hospital beds, medical equipment, etc.) are geocoded and analysed by the response engine 100 to provide needed information, such as the identification of future infectious disease hot zones location and quantity of ventilators as part of the response; low risk zones that may be re-opened safely, i.e., public gatherings and commercial activity may be resumed, relative to a broad re-opening of the economy; as well as other socioeconomic outcomes. The response engine 100 may identify, e.g., which location needs ventilators and/or other medical devices, where people may be at risk to varying degrees, geographical areas at risk of being affected by the infectious disease to varying degrees, the availability of the ventilators in a particular geographical area, etc. The response engine 100 may provide history data on healthcare resources and/or history data on environmental data (e.g., climate, temperature, etc.) to identify growing and changing health-care needs for the overall population on varying scales of community.

The response engine 100 may further generate a Health Risk Index (HRI) to provide health information on disease/disaster-impacted populations to first responders. The HRI may help to determine an impacted population based on the provided health information so that the medical and health needs may be addressed during response efforts. The response engine 100 may also identify future needs when a community changes (include the changes to risk factors of the community), allowing a health system to ensure its capacity and resource levels can continue to meet healthcare needs for various diseases. The response engine 100 may also facilitate better allocation of both health and social resources to disadvantaged and at-risk communities to help mitigate and address health care inequities.

FIG. 2 is a schematic diagram of a processing system 200, according to at least one example embodiment described herein. In one or more embodiments, the processing system 200 may be the process system 120 of FIG. 1. The processing system 200 may include one or more processors or computing devices 123 (collectively, "processor" as used herein), a system memory 125, communication ports 127 to acquire data from one or more of data sources 110, and a database 129. Processing system 200 may be configured and arranged to implement an information system platform with a data analytic engine (such as the response engine) as discussed below. Data acquired from the data sources 110 may be added to the database 129. The stored data may be analysed using data analytics, and formatted for output for any suitable purpose, including for display on a geographic or other map via display 130, or for further analysis or review (e.g., personal or machine) either locally or remotely (e.g., into the EHR system at a hospital or other healthcare service provider 140).

FIG. 3 shows an example map generated by an advanced smart pandemic and infectious disease response engine, according to at least one example embodiment described herein.

FIG. 4 shows another example map generated by an advanced smart pandemic and infectious disease response engine, according to at least one example embodiment described herein.

The example maps generated by the advanced smart pandemic and infectious disease response engine disclosed herein may show a prediction of a spread of an infectious disease (e.g., SARS, COVID-19) and serve as a tool for assessing the allocation and/or availability of pandemic response resources (e.g., doctors, nurses, beds, test kits, ventilators, personal protective equipment (PPE) such as non-surgical masks, surgical masks, gowns, gloves, etc.) and for predicting risk areas of the infectious disease, of varying degrees of risk, and for illustrating hot zones in accordance with at least some embodiments described herein.

In one or more embodiments, FIG. 3 may indicate, based on the data obtained from data sources 110, regions with the number of confirmed/positive diagnoses (or diagnoses related to whatever health risk is being tracked), the number of death related to the disease, and the number of counties being impacted in the U.S. (or any state or region of the country, as well as regions outside the country that may be of interest) by the shaded areas (showing the Transmission Risk Index) and by the solid dots (showing the counties being impacted), such information being made available by public sources.

FIG. 4 may indicate, based on the data obtained from data sources 110, regions with the number of confirmed/positive diagnoses (or diagnoses related to whatever risk is being tracked), the number of deaths related to the disease, and the number of ventilators available in a city in, e.g., Maryland (or any other state or region of the country, as well as regions outside the country that may be of interest) by the shaded areas (showing the Transmission Risk Index) and locations of treatment facilities by the crosses, and medical facilities with ventilators (including Hospitals) by the solid dots, such information being made available by public sources. FIGS. 3 and 4, illustrate but examples of how many health resources (e.g., ventilators) are available and how many confirmed patients/cases and death in a given period of time.

The advanced smart pandemic and infectious disease response engine 100 provides spatial data infrastructure including geospatial visualization capabilities, machine learning and Artificial Intelligence (AI) based predictive analytics, and data sets from data sources 110.

FIGS. 3 and 4, of course, illustrate but examples of how the mapping may provide a ready visualization of the physical proximity of treatment facilities to areas of greater risk, availability of travel routes from such hot zones to the treatment facilities, political boundaries where local agencies or representatives may be targeted, etc. With knowledge of demographic, economic, and other social determinants, relationships between and among the subject population and social determinants are also readily ascertained by this visual presentation, much more effectively than mere data manipulation or mental analysis, which may not be effectively performed for the myriad and disparate data, data sources, and correlations that form the foundation for the hot zone maps shown in FIGS. 3 and 4.

The response engine 100 may create a Transmission Risk Index (TRI) at the state/national/international and local levels to track the infectious disease flow and identify at-risk areas for potential future spread of contagion. The TRI identifies the high risk areas as well as assesses the environmental factors that may potentially exacerbate or inhibit the viral transmission (e.g., incubation temperature for viral replication, etc.). The TRI may be used to make recommendations to the community on areas that should be considered for social distancing or quarantine measures as well as communities or public areas that should be decontaminated. The response engine 100 may facilitate tracking e.g., occupancy rates for healthcare facilities (such as hospitals and surgical centers) and the utilization of medical resources (such as MRI machines, ventilators, and critical medications, etc.).

The response engine 100 may create the TRI to predict the location of future outbreaks of the disease, and may create a Mortality Risk Index to identify the regions with the highest risk of critical illness and death due to the disease—each at the county, ZIP code, and census tract levels. These Indices (TRI, Mortality Risk Index, etc.) may allow emergency managers and medical responders to predict the next hot zones and outbreaks of the disease at the county and/or ZIP Codes levels. The prediction may be based on current cases, disease progression, mobility, and/or social data within the response engine 100. The output of the response engine (TRI, Mortality Risk Index, etc.) may enable deployment of e.g., medical resources in advance of the viral outbreaks, rather than chasing the outbreaks, to aid e.g., first responders to save lives, and may improve the ability to halt the spread of the contagion and treat the infected.

These Indices may guide e.g., eventual de-quarantine efforts to resume economic activity in "safe" or "low risk" zones, to reduce the risk of a second bump (or second wave) of cases as normal activity and social interaction is resumed, to speed the safe resumption of normal economic activity and benefit the economy, and to resume normal activities and reduce the mental health risk associated with long-term social isolation.

These Indices may facilitate understanding of disruptions and availability in supply chain of medical supplies and equipment, may help to provide information on on-the-ground medical facilities and key resources and equipment, such as ventilators, masks, and other PPE, needed during emergency response as well as recovery phases, and may help to develop supply chains visibility so key resources and equipment can be acquired, manufactured, allocated from other areas, or other contingencies can be developed.

These Indices may help to anticipate downstream impact and strain on industries and the social safety net, may help assess downstream impacts from pandemic to ensure continuity of critical services (for example, funeral homes are an industry potentially impacted by a surge in the COVID-19 fatalities).

FIG. 5 shows an example processing flow 500 for a response engine to generate a pandemic predictive model, according to at least one example embodiment described herein. In one or more embodiments, the model uses general population data (e.g., at a geographic area such as a city/town, a state/province, a country, etc.) to identify patients who have tested positive for the subject infectious disease (with no or mild symptoms, with severe symptoms warrant hospitalization, with severe symptoms that warrant intensive care (ICU), etc.), and patients who have tested negative for the subject infectious disease (have developed an antibody (recovered from the subject infectious disease), have not developed an antibody, etc.). It will be appreciated that in the figures described herein, the data flow through the blocks may be recursive instead of unidirectional.

Processing flow 500 may include one or more operations, actions, or functions depicted by one or more blocks 510, 520, 530, 540, 550, 560, 570, and 580. Although illustrated as discrete blocks, various blocks may be divided into additional blocks, combined into fewer blocks, or eliminated, depending on the desired implementation. As a non-limiting example, the description of processing flow 500, corresponding to the depiction thereof in FIG. 5 and performed by processing system 120 in one or more embodiments described herein, pertains to predicting patients affected by the infectious disease under a certain condition. Processing may begin at blocks 510 and 580.

Block 510 (Acquire Population Data) may refer to processing system 120 receiving a set of population data from data sources 110 via communication ports 127. Population data may include a form of identification of individual patients or potential patients of the infectious disease, including but not limited to wireless or wired communications from data sources 110 or manual entry (for example, by an operator using a keyboard or tablet, smartphone, etc. utilizing appropriate application software). In some embodiments, and without limitation, the population data may be obtained from public sources such as a government agency, healthcare service providers such as hospitals, Centers for Disease Control (CDC), etc. Block 510 may be followed by either of Block 520 and Block 530.

Block 580 (Acquire Condition Data) may refer to processing system 120 receiving a set of condition data from data sources 110 via communication ports 127. Condition data may include a location of the patients or potential patients of the infectious disease, an incubation temperature for viral replication, a transmission risk index for the infectious disease, including but not limited to wireless or wired communications from data sources 110 or manual entry (for example, by an operator using a keyboard or tablet, smartphone, etc. utilizing appropriate application software). In some embodiments, and without limitation, the condition data may be obtained from public sources such as the government agency, the Centers for Disease Control, etc. Block 580 may be followed by Block 540.

Block 520 (Identify First Subset) may refer to processor 123 identifying a first subset of the set of population data based on at least one criterion in which the first subset includes patients who tested positive for the subject infectious disease and are undergoing treatment (hospitalized or admitted to intensive care unit (ICU) or claimed dead) or quarantine (with no or mild symptom), in the examples given. The first subset may include a statistically significant percentage of patients. This data may be obtained from a government agency, healthcare service providers such as hospitals, the CDC, by way of non-limiting examples. Block 520 may be followed by Block 540.

Block 530 (Identify Second Subset) may refer to processor 123 applying a predictive model to perform a retrospective analysis of the set of population data to identify a second subset of the set of population data in which the second subset includes patients who have at least likely developed an antibody (recovered from the infectious disease) based on the first subset and the condition data. For example, the model may produce a risk score for each individual in the population data and identify those individuals who would not be considered to be at risk for the infectious disease in a particular location and/or under an incubation temperature for viral replication and/or with a predetermined transmission risk index for the infectious disease. Block 530 may be followed by Block 540.

It will be appreciated that the second subset data can be obtained by, for example, conducting extensive antibody test for each individual in the set of population data. It will also be appreciated that in at least one example embodiment, the first subset may be utilized in Block 530 and the second subset may be utilized in Block 510. In such embodiments, the predictive model may be utilized to perform a retrospective analysis of the set of population data to identify the first subset of the set of population data based on the second subset and the condition data. For example, the model may produce a risk score for each individual included in the population data and identify those individuals who would be considered to be at risk for the infectious disease in a particular location and/or under an incubation temperature for viral replication and/or with a predetermined transmission risk index for the infectious disease.

In one or more embodiments, the predictive model may have a plurality of analyser channels (customized for the infectious disease), each of which corresponds to an observable condition of a patient. The channels may be weighted to customize or fine tune the predictive model, signifying whether any channels are of equal or greater/lesser importance than others in identifying the first subset or second subset patient.

Predictive modelling may allow allocation of channel points in accordance with, or independent of, channel weighting based on the statistical sensitivity of specific factors in predicting, for example, a patient in either of the first subset or second subset. For example, a base score may be calculated as the summation of points attributed to the (weighted or unweighted) analyser channels. The analyser channels may be broken down further into analyser features that provide additional sensitivity in identifying individuals who may be at high/low risk of being affected by the infectious disease.

In one or more embodiments, points and/or weights may be assigned to each channel. It should be noted that not all of the channels or features need be part of any given analysis. Moreover, other channels and/or features may be suitable in addition or in the alternative, depending on the study or analysis. In one or more embodiments, point modifiers may be applied to one or more of the channels and/or features to affect the influence of the same on the total base score. Non-limiting examples include percentage weightings, inclusion/exclusion of certain channels/features to suit any particular analysis or subject population, etc.

In one or more embodiments, the model may place a higher weight or point value for any or all of the channels. In other words, whether certain conditions place a patient at greater risk of being affected by the infectious disease in a long term care facility in contrast to a private residence may be considered. For example, whether an aggregated long term care facility is worse than a low or medium density private residence may be considered in the model. Accordingly, informed guidance may be given towards allocation of health care resources and/or towards implementing more rigorous measurements at long term care facilities. Block 520, 530, and 580 may be followed by Block 540.

Block 540 (Determine Correlation between First/Second Subsets) may refer to processor 123 determining a correlation between the first subset identified in Block 520 and the second subset identified in Block 530 under the conditions acquired at Block 580. The correlation may be any suitable correlation that results in a value that may be compared to a threshold value. For example, in one or more embodiments, processor 123 may calculate a mathematical correlation between the first subset and the second subset under a certain condition. Additionally or alternatively, in one or more embodiments, processor 123 may determine which individuals in the first subset are also in the second subset and compare the result to a threshold. Block 540 may be followed by Block 550.

Block 550 (Does Correlation Meet or Exceed a Predetermined Threshold?) may refer to processor 123 determining whether the result of Block 540 exceeds a predetermined threshold. If so, then Block 560 may follow Block 550. If not, then Block 570 may follow Block 550.

Block 560 (Output the Model) may refer to processor 123 outputting the predictive model for, e.g., incorporation into a healthcare records system such as EHR or any other suitable systems/platforms, as the model may be considered to be valid for implementation in determining whether a subject patient may be at risk of being affected by the infectious disease.

Block 570 (Adjust Model) may refer to one or more channels being modified, deleted, or added to the predictive model (starting from an initial model, e.g., in a recursive algorithm) and fed back to Block 530 for re-testing in an iterative process performed until Block 550 is answered "YES." For example, a channel may be modified by adding points or point multipliers, or by changing or adding the weighting. It will be appreciated that the channel may be modified by adding new data, changing the processing of the existing data, and/or deploying new ways to process data.

The base score may be adjusted based on several variables in order to obtain a risk score used to modify a clinician's behaviour, for example. In one or more embodiments, a positive adjustment may be made based on the number of total active channels as well as having channels with greater than five active analyser features. A negative adjustment may be made for single active channels as well as for having fewer than five active features among all analyser channels. Additional positive adjustments may be made in accordance with, e.g., a natural language processing (NLP), for analyser features having grammatical phrases of greater than four words. In one or more embodiments, the composite score may be the sum of the base points and adjustment points, although other combinations of these and/or other variables may be employed additionally or as modifications to the above.

FIG. 6 shows an example processing flow 600 for a response engine to track resource levels, according to at least one example embodiment described herein. In one or more embodiments, the model uses patients' data, e.g., patients who have tested positive for the infectious disease (with no or mild symptoms, with severe symptoms that warrant hospitalization, with severe symptoms that warrant admission to an ICU, etc.), and/or patients who have tested negative for the infectious disease (have developed an antibody (recovered from the infectious disease), have not developed an antibody, etc.) to identify patients that currently need healthcare resources. The model also uses resource data (e.g., the location, quantity, and/or availability of doctors, nurses, beds, test kits, ventilators, personal protective equipment (PPE), masks, gloves, MRI machines, critical medications, etc.) to identify resource levels (e.g., availability, location, quantity, etc.).

Processing flow 600 may include one or more operations, actions, or functions depicted by one or more blocks 610, 620, 630, 640, and 650. Although illustrated as discrete blocks, various blocks may be divided into additional blocks, combined into fewer blocks, or eliminated, depending on the desired implementation. As a non-limiting example, the description of processing flow 600, corresponding to the depiction thereof in FIG. 6 and performed by processing system 120 in one or more embodiments described herein, pertains to predicting resource levels under a certain condition (e.g., for a particular location, etc.), so that the capacity and resources of the healthcare system is not overwhelmed. Processing may begin at blocks 610 and 620.

Block 610 (Acquire Patient Data) may refer to processing system 120 receiving a set of patient data from data sources 110 via communication ports 127. The data acquired in Block 610 may include, without limitation, identification of patients who have tested positive for the infectious disease (with no or mild symptoms, with severe symptoms that warrant hospitalization, with severe symptoms that warrant admission to an ICU, etc.), and/or patients tested negative for the infectious disease (have developed an antibody (recovered from the infectious disease), have not developed an antibody, etc.). The data may be acquired via wireless or wired communications from data sources 110 or manual entry (for example, by an operator using a keyboard or tablet, smartphone, etc. utilizing appropriate application software). In some embodiments, and without limitation, the patient data may be obtained from public sources such as the government agency, the healthcare service providers such as the hospitals, the Centers for Disease Control, etc. Block 610 may be followed by Block 630.

Block 620 (Acquire Resource Data) may refer to processing system 120 receiving a set of resource data from data sources 110 via communication ports 127. The data acquired in Block 620 may include, without limitation, the location, quantity, and/or availability of doctors, nurses, beds, test kits, ventilators, personal protective equipment (PPE), masks, gloves, MRI machines, critical medications, etc., acquired via wireless or wired communications from data sources 110 or manual entry (for example, by an operator using a keyboard or tablet, smartphone, etc. utilizing appropriate application software). In some embodiments, and without limitation, the resource data may be obtained from public sources such as the government agency, the healthcare service providers such as the hospitals, the Centers for Disease Control, etc. Block 620 may be followed by Block 630.

Block 630 (Apply Model) may refer to processor 123 analysing the data acquired in Blocks 320 and 330 in accordance with the model validated according to procedure 500 and outputted at Block 560. For example, the data in each analyser channel may be converted to a channel score. Block 630 may be followed by Block 640. It will be appreciated that Block 630 also includes geocoding the data (e.g., the patient and the resource data), loading the data into a geospatial data analytic application (or spatial data infrastructure) including the model, and applying the model to the data.

Block 640 (Determine Resource Levels) may refer to processor 123 determining resource levels based on the channel scores determined in Blocks 640. For example, the channel scores may be summed to create resource levels. The resource levels may indicate the availability (e.g., the number of a resource that is available for use and/or that is needed) of a particular resource (e.g., ventilators) in a given period of time (day, week, month, etc.) in view of the patient data (patients that need the particular resource). Block 640 may be followed by Block 650.

Block 650 (Trigger Resource Procurement) may refer to processor 123 triggering a resource allocation and/or procurement based on the determined resource levels in Blocks 640. For example, if the resource levels data of Block 640 is less than a predetermined threshold, a resource allocation and/or procurement (and/or an alert to the display/system) is triggered for that particular resource. Block 650 may be followed by Block 620 to adjust the resource data based on the resource allocation and/or procurement of Block 650.

FIG. 7 shows an example processing flow 700 for a response engine to facilitate generating quarantine and/or de-quarantine plans, according to at least one example embodiment described herein. In one or more embodiments, the model uses a first set of patient data (high risk patient or high risk of transmission) including identification of, e.g., patients who have tested positive for the infectious disease (with no or mild symptoms, with severe symptoms that warrant hospitalization, with severe symptoms that warrant admission to an ICU, etc.), and a second set of patient data (low risk patient or low risk of transmission), e.g., patients who have tested negative for the infectious disease (have developed an antibody (recovered from the infectious disease), have not developed an antibody, etc.) to generate quarantine and/or de-quarantine plans. The model also uses condition data (location of the patients or potential patients of the infectious disease; an incubation temperature, humidity, and/or other environmental factors for viral replication; a transmission risk index for the infectious disease, etc.) to generate quarantine and/or de-quarantine plans.

Processing flow 700 may include one or more operations, actions, or functions depicted by one or more blocks 710, 720, 730, 740, 750, and 760. Although illustrated as discrete blocks, various blocks may be divided into additional blocks, combined into fewer blocks, or eliminated, depending on the desired implementation. As a non-limiting example, the description of processing flow 700, corresponding to the depiction thereof in FIG. 7 and performed by processing system 120 in one or more embodiments described herein, pertains to generating quarantine and/or de-quarantine plans under a certain condition (e.g., for a particular location, under a certain temperature, etc.). Processing may begin at blocks 710, 720, and 730.

Block 710 (Acquire High Risk Patient Data) may refer to processing system 120 receiving a first set of patient data from data sources 110 via communication ports 127. The data acquired in Block 710 may include, without limitation, identification of patients who have tested positive for the infectious disease (with no or mild symptoms, with severe symptoms that warrant hospitalization, with severe symptoms that warrant admission to an ICU, etc.). The data may be acquired via wireless or wired communications from data sources 110 or manual entry (for example, by an operator using a keyboard or tablet, smartphone, etc. utilizing appropriate application software). The data acquired in Block 710 are patients with high risk of transmission of the infectious disease. In some embodiments, and without limitation, the patient data may be obtained from public sources such as the government agency, the healthcare service providers such as the hospitals, the Centers for Disease Control, etc. Block 710 may be followed by Block 740.

Block 720 (Acquire Low Risk Patient Data) may refer to processing system 120 receiving a second set of patient data from data sources 110 via communication ports 127. The data acquired in Block 720 may include, without limitation, identification of patients who have tested negative for the infectious disease (have developed an antibody (recovered from the infectious disease), have not developed an antibody, etc.). The data acquired in Block 720 are patients with low risk of transmission of the infectious disease, and the data may be acquired via wireless or wired communications from data sources 110 or manual entry (for example, by an operator using a keyboard or tablet, smartphone, etc. utilizing appropriate application software). In some embodiments, and without limitation, the patient data may be obtained from public sources such as the government agency, the healthcare service providers such as the hospitals, the Centers for Disease Control, etc. Block 720 may be followed by Block 740.

Block 730 (Acquire Condition Data) may refer to processing system 120 receiving a set of condition data from data sources 110 via communication ports 127. The data acquired in Block 730 may include location of the patients or potential patients of the infectious disease, an incubation temperature for viral replication, a transmission risk index for the infectious disease. The data may be acquired via wireless or wired communications from data sources 110 or manual entry (for example, by an operator using a keyboard or tablet, smartphone, etc. utilizing appropriate application software). In some embodiments, and without limitation, the condition data may be obtained from public sources such as the government agency, the Centers for Disease Control, etc. It will be appreciated that in Blocks 710, 720, and/or 730, the data used may incorporate all the health data, social data, environmental data, economic data, and/or behavioural data, etc. Block 730 may be followed by Block 740.

Block 740 (Apply Model) may refer to processor 123 analysing the data acquired in Blocks 710, 720, and 730 in accordance with the model validated according to procedure 500 and outputted at Block 560. For example, the data in each analyser channel may be converted to a channel score. Block 740 may be followed by Blocks 750 and/or 760.

Block 750 (Generate Quarantine Actions) may refer to processor 123 generating plans for quarantine based on the channel scores determined in Blocks 740. For example, the channel scores may be summed to create quarantine plans. The quarantine plans include monitoring and guiding the high risk patients under social isolation and/or quarantine for given period of time (day, week, month, etc.), and the given period of time may be up to and including the duration of the pandemic and recovery phases. Block 750 may be followed by Block 710 to adjust the high risk patient data after the quarantine plans are implemented.

Block 760 (Generate De-quarantine Actions) may refer to processor 123 generating plans for de-quarantine based on the channel scores determined in Blocks 740. For example, the channel scores may be summed to create de-quarantine plans. The de-quarantine plans include developing plan for structured de-quarantine of all impacted communities for low risk patients. Block 760 may be followed by Block 720 to adjust the low risk patient data after the de-quarantine plans are implemented.

FIG. 8 illustrates at least one computer program product that may be utilized to provide an advanced smart pandemic and infectious disease response engine, according to at least one example embodiment described herein. Program product 800 may include a signal bearing medium 802. Signal bearing medium 802 may include one or more instructions 804 that, when executed by, for example, a processor, may provide the functionality described above with respect to FIGS. 5-7. By way of example, but not limitation, instructions 804 may include: one or more instructions for patient data and resource data, one or more instructions for population data and condition data, one or more instructions for applying the predictive model to the input data, one or more instructions for determining and outputting the output data of the predictive model, one or more instructions for adjusting the predictive model/data, one or more instructions for outputting/generating the model, etc. Thus, for example, referring to FIGS. 5-7, processor 123 may undertake one or more of the blocks shown in FIGS. 5-7 in response to instructions 804.

In some implementations, signal bearing medium 802 may encompass a computer-readable medium 806, such as, but not limited to, a hard disk drive, a CD, a DVD, a flash drive, memory, etc. In some implementations, signal bearing medium 802 may encompass a recordable medium 808, such as, but not limited to, memory, read/write (R/W) CDs, R/W DVDs, etc. In some implementations, signal bearing medium 802 may encompass a communications medium 810, such as, but not limited to, a digital and/or an analog communication medium (e.g., a fiber optic cable, a waveguide, a wired communications link, a wireless communication link, etc.). Thus, for example, computer program product 800 may be conveyed to one or more modules of processor 123 by an RF signal bearing medium, where the signal bearing medium is conveyed by a wireless communications medium (e.g., a wireless communications medium conforming with the IEEE 802.11 standard).

FIG. 9 shows a block diagram illustrating an example computing device 900 by which various example solutions described herein may be implemented, according to at least one example embodiment described herein. In a very basic configuration 902, computing device 900 typically includes one or more processors 904 and a system memory 906. A memory bus 908 may be used for communicating between processor 904 and system memory 906.

Depending on the desired configuration, processor 904 may be of any type including but not limited to a microprocessor (µP), a microcontroller (µC), a digital signal processor (DSP), or any combination thereof. Processor 904 may include one or more levels of caching, such as a level one cache 910 and a level two cache 912, a processor core 914, and registers 916. An example processor core 914 may include an arithmetic logic unit (ALU), a floating point unit (FPU), a digital signal processing core (DSP Core), or any combination thereof. An example memory controller 918 may also be used with processor 904, or in some implementations memory controller 918 may be an internal part of processor 904.

Depending on the desired configuration, system memory 906 may be of any type including but not limited to volatile memory (such as RAM), non-volatile memory (such as ROM, flash memory, etc.) or any combination thereof. System memory 906 may include an operating system 920, one or more applications 922, and program data 924. Application 922 may include instructions 926 to carry out predicting a spread of an infectious disease and evaluating pandemic response resources, and predicting and responding to risk areas of the infectious disease that are arranged to perform functions as described herein including those described with respect to process 500, 600, 700 of FIGS. 5-7. Program data 924 may include data (e.g., population, patient, resource, condition, etc.) from data resources 110 that may be useful for the response engine as is described herein. In some embodiments, application 922 may be arranged to operate with program data 924 on operating system 920 such that implementations of the response engine in, e.g., healthcare systems to assist clinicians in treating patients in clinical settings and post-examination or discharge, may be provided as described herein. This described basic configuration 902 is illustrated in FIG. 9 by those components within the inner dashed line.

Computing device 900 may have additional features or functionality, and additional interfaces to facilitate communications between basic configuration 902 and any required devices and interfaces. For example, a bus/interface controller 930 may be used to facilitate communications between basic configuration 902 and one or more data storage devices 932 via a storage interface bus 934. Data storage devices 932 may be removable storage devices 936, non-removable storage devices 938, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and non-volatile, removable and non-removable media implemented in any method or technology for storage of information, such as computer readable instructions, data structures, program modules, or other data.

System memory 906, removable storage devices 936 and non-removable storage devices 938 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 900. Any such computer storage media may be part of computing device 900.

Computing device 900 may also include an interface bus 940 for facilitating communication from various interface devices (e.g., output devices 942, peripheral interfaces 944, and communication devices 946) to basic configuration 902 via bus/interface controller 930. Example output devices 942 include a graphics processing unit 948 and an audio processing unit 950, which may be configured to communicate to various external devices such as a display or speakers via one or more A/V ports 952. Example peripheral interfaces 944 include a serial interface controller 954 or a parallel interface controller 956, which may be configured to communicate with external devices such as input devices (e.g., keyboard, mouse, pen, voice input device, touch input device, etc.) or other peripheral devices (e.g., printer, scanner, etc.) via one or more I/O ports 958. An example communication device 946 includes a network controller 960, which may be arranged to facilitate communications with one or more other computing devices 962 over a network communication link via one or more communication ports 964.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 900 may be implemented as a portion of a small-form factor portable (or mobile) electronic device such as a cell phone, a tablet, a personal data assistant (PDA), a personal media player device, a wireless web-watch device, a personal headset device, an application specific device, or a hybrid device that include any of the above functions. Computing device 900 may also be implemented as a personal computer including both laptop computer and non-laptop computer configurations.

FIG. 10 illustrate a work flow 1000 of an advanced smart pandemic and infectious disease response engine, according to at least one example embodiment described herein.

As shown in FIG. 10, Blocks 1010, 1020, 1030, 1040, and 1090 represent inputs to the response engine; Blocks 1050, 1060, 1070, and 1080 represent outputs of the response engine, and Blocks 1100, 1110, and 1120 represent users of the output of the response engine. It will be appreciated that the input Blocks 1010, 1020, 1030, 1040, and 1090 can be e.g., data sources 110*a* . . . *n* of FIG. 1; and the users Blocks 1100, 1110, and 1120 can be e.g., the users 140, 150 of FIG. 1. Other inputs data may include e.g., mobility infrastructure data such as airports data, public transit data, metros data, etc. Input data may also include e.g., behavioral data such as drinking history, smoking history, etc. Input data may further include e.g., environmental data such as air quality data, temperature data, humidity data, etc.

In at least one example embodiment, Block 1010 represents health data, including disease (e.g., COVID-19) case statistics, critical conditions, hospitals, medical facilities, insurance, medical equipment, and other medical resources. Blocks 1020 and 1030 represent social data including population demographics, population density, socio-economic status, housing, education, etc.

In at least one example embodiment, Block 1050 represents cases of the disease by population in a particular area, Block 1060 represents Mortality Risk Index of the disease, Block 1070 represents geographic weighting of the disease, and Block 1080 represents TRI of the disease. In at least one example embodiment, the accessibility of the output Blocks 1050, 1060, 1070, and 1080 of the response engine include online access of the response engine, web browser, and mobile devices. The output may be open to public and/or licensed to specific users; output data sets may be available through the application programming interfaces, the web feature services, the web map services, and/or direct download. The response engine provides friendly user interface to visualize and query data, may be hosted on web services, and may be replicated in a local environment for additional privacy and security.

PPE needs may vary during different phases of a pandemic. To constructively identify PPE needs for a potential pandemic or wide-spread health emergency, planners may consider that a pandemic lifecycle may be divided into three or more phases. The phases of a pandemic lifecycle include a pre-pandemic or planning phase, which may be a time period between the discovery of a potential pandemic-causing contagious disease anywhere in the world and its local arrival marked by the first patient so-diagnosed within a threshold vicinity. The next phase of a pandemic lifecycle includes a pandemic response phase, which may be a time period at which active measures to combat and control the spread of the pandemic and to treat the infected patients begin. The third phase of a pandemic lifecycle include a pandemic recovery phase, which may begin when local and national economies begin to reopen, while social distancing and other guidelines (e.g., the wearing of PPE such as masks, gloves, etc.) intended to slow the spread of the pandemic and other efforts to treat the infected patients remain in place. A post-pandemic phase may be considered to have begun when at least a significant proportion of efforts related to pandemic control have stopped and PPE needs have returned to pre-pandemic levels.

As disclosed and recited herein, PPE needs may vary depending on the current phase of the pandemic lifecycle. In accordance with embodiments recited and disclosed herein, PPE needs may be predicted based on e.g., number and type of healthcare and essential workforces, number of active cases (e.g., current number of patients infected by pathogens such as COVID-19, etc.), transmission risk and mortality risk indices for each phase of the pandemic, etc. Embodiments disclosed herein may produce a risk-based range of PPE needs by item/type at different consumption rates, including, but not limited to, e.g., a low (or first) PPE burn rate (hereinafter "low PPE rate"), a high (or second) PPE burn rate (hereinafter "high PPE rate"), and an index PPE burn rate (hereinafter "index PPE rate"). With the risk-based range of PPE needs, users such as PPE buyers (including health systems and emergency stockpile managers, etc.) may be able to predict their PPE needs for a pandemic or wide-spread health emergency based on the burn rate applicable to the users and allow the users to make a risk-based decision for the purchase and acquisition of PPE.

Table 1 below shows the burn rates of the most common PPE for users such as health care workers and law enforcement personnel. The PPE burn rates for each type of PPE for each user (e.g., health care workers, law enforcement personnel, etc.) may be obtained from input data sources (see e.g., FIGS. 10-15). Hereafter, the PPE burn rates for each type of PPE for each user may be referred to as "low burn rate" (or "first burn rate", i.e., minimum daily PPE consumption amount) and "high burn rate" (or "second burn rate", i.e., maximum daily PPE consumption amount). It will be appreciated that in an embodiment, Table 1 is based on research conducted among the healthcare, EMS, and/or law enforcement community in the early days of the pandemic. The data are exemplary and may subject to changes based on factors including changes in user habits and behaviours, personal illness, disease severity, availability of PPE, government mandates, etc.

TABLE 1

| PPE | HealthCare Workers | | Law Enforcement | |
|---|---|---|---|---|
| | Low Burn Rate | High Burn Rate | Low Burn Rate | High Burn Rate |
| Non-Surgical Masks | 2 | 25 | 1 | 12 |
| Surgical Masks | 4 | 25 | 1 | 12 |
| Gowns | 6 | 50 | 0 | 0 |
| Gloves | 12 | 75 | 12 | 75 |

Low PPE rate, high PPE rate, and/or index PPE rates are determined, at least in part, to facilitate predictions or estimates of risk-based range of PPE needs. A low PPE rate (i.e., minimum PPE consumption amount for an organization or an area in a period of time) may be determined as:

$$\text{Essential Workforce} * \text{Constant} * \frac{(\text{Hospitalization Rate} * \text{Active Cases})}{\text{Total Staffed Beds}} * \text{Low Burn Rate of each } PPE$$

A high PPE rate (i.e., maximum PPE consumption amount for an organization or an area in a period of time) may be determined as:

$$\text{Essential Workforce} * \text{Constant} * \frac{(\text{Hospitalization Rate} * \text{Active Cases})}{\text{Total Staffed Beds}} * \text{High Burn Rate of each } PPE$$

Essential Workforce, used to determine both a low PPE rate and a high PPE rate as listed above, may refer to e.g., the Census-reported number of primary health care personnel, police, firefighters, emergency medical services personnel, etc. within one or more particular health-care related organizations or within one or more specified geographic areas. Essential Workforce takes into account that PPE is to be used by people.

"Constant," used to determine both a low PPE rate and a high PPE rate as listed above, may refer to any suitable constant. In one embodiment, the constant may be 5/7 to account for a five-day work week. In such case, the period of time (for the low/high PPE rate) is a week. It will be appreciated that the period of time may be a day, a week, a month, etc. The constant may be adjusted for workforces that operate by shifts or work a different number of days per week. It will also be appreciated that users may keep a balance between overly responsive and timely reporting regarding PPE estimates. For example, daily predictions may be overly responsive and monthly predictions may not be timely. Using a seven-day (a week, i.e., setting the constant to 5/7) a running average may provide an optimal prediction on the PPE needs. It will be appreciated that the running average may be subject to change (e.g., depending on the rate of change of PPE needs and/or the delivery capabilities of PPE suppliers, and/or any other suitable changes. Embodiments disclosed herein provide flexibility to accommodate any of such changes.

The component ((Hospitalization Rate*Active Cases)/ Total Staffed Beds), used to determine both a low PPE rate and a high PPE rate as listed above, produces a component that may refer to the proportion of hospitalizations attributed to pathogens (such as COVID-19, etc.) relative to overall capacity of a particular facility or particular geographic area. This component may act as a proxy for a severity of the pandemic. This component is essential for estimating PPE needs since PPE is intended to protect the wearer from exposure to and therefore from spreading (in this case) viral contagion. As such, a key component to the PPE needs assessment is the amount of viral load to which the wearer may potentially be exposed. Hospitals with a lower viral load (e.g., through fewer COVID-19 patients) will need less PPE, and vice versa. Hospitalization Rate may refer to a percentage of active patients that require hospitalization, active cases may refer to the total number of infected patients who are considered to be contagious or likely to be contagious after incubation period, and total staffed beds may refer to the capacity (e.g., beds with healthcare staff to support) of the facility or geographic area.

A Low Rate of each PPE may refer to an estimated/ predicted minimum number of each PPE type (such as masks, gowns, pair of gloves, etc.) used per essential/health worker per day. See Table 1.

A High Rate of each PPE may refer to an estimated/ predicted maximum number of each PPE type used per essential/health worker per day. See Table 1.

The Index PPE rate (i.e., PPE consumption amount predicted or estimated with a pandemic risk index for an organization, a facility, or within a particular geographic area in a period of time) may be determined as:

$$\frac{(\text{Pandemic Risk Index} * (\text{High } PPE \text{ Rate} - \text{Low } PPE \text{ Rate}))}{100} + \text{Low Burn Rate}$$

The Pandemic Risk Index is a combination of a Mortality Risk Index and a Transmission Risk Index. In an embodiment, the values of the Pandemic Risk Index may range from 0 to 100. The Pandemic Risk Index may be determined as:

Pandemic Risk Index Transmission index*Mortality Risk Index.

The Transmission Risk Index may be used to predict the spread and locations of future outbreaks at multiple geographic levels, including global, regional (e.g., multiple geographically adjacent countries, such as Central America, Sub-Saharan Africa, Polynesia, etc.), country, state, county, ZIP Code, census tract, and/or health system levels, etc. The Transmission Risk Index may be determined as:

$$\text{Transmission Risk Index} =$$

$$\frac{(\text{Case Density} + \text{Case Density } IDW + \text{Case Density Mobility})}{3}$$

The Case Density is the number of cases (patient infected) per 100,000 people per 100 square miles. The Case Density may be determined as:

$$\text{Case Density} = \frac{\left\{ \frac{\text{cases} * (1 + (\text{average percent increase in daily cases over the past week}))}{(\text{total population}/100000)} \right\}}{(\text{area (in 100 square miles)})}$$

Case Density IDW may be used to determine an Inverse Distance Weight (IDW) for each geography e.g. using 8 (or other predetermined numbers) nearest neighbours for counties and 16 (or other predetermined numbers) nearest neighbours for ZIP Codes. The Case Density IDW is an average of the weights multiplied by the Case Density for each geography. As defined herein, the term "weights" may refer to a distance between the centroid (e.g., center point) of the geography (e.g., the county for which the risk index is established) and its neighbouring counties' centroids. It will be appreciated that IDW may refer to a type of deterministic method for multivariate interpolation with a known scattered set of points. As defined herein, the term "scattered set of points" may refer to a set of centroids of each geometry. As defined herein, the term "centroids" may refer to a center of land mass of the geometry (e.g., county) that may be either within or outside the geometry. As an example of a centroid that is outside the geometry: the centroid for a "C" shaped county may lie in the middle of the "C", which may be outside the boundary of the county. The centroid may also be determined as the center of population mass of the geometry, e.g., the overall population center of the county. The assigned values to unknown points may be calculated with a weighted average of the values available at the known points. IDW applies the weighted average, and resorts to the inverse of the distance to each known point ("amount of proximity") when assigning weights.

Case Density Mobility takes into account e.g., highway/car, air, bus, and/or metro routes, etc. Case Density Mobility is determined by taking an average (a route average) of all of the Case Densities from all of the ZIP Codes that each individual route passes through and then taking an average (a second average) of the route average and the actual count (e.g., Case Density) of each individual zip code. For instance, where there are multiple routes in one ZIP Code, the Case Density Mobility represents the average of all those route averages and the value of the individual ZIP Code. The second average is then multiplied by the Mobility factors as determined by adherence to social distancing regulations. For example, Google Mobility Report is produced for many countries, and in the U.S. at the County level. See https://www.googe.com/covid19/mobility/. As defined herein, the term "Mobility factors" may refer to factors that indicate the movement of people with respect to transit, including commuter miles driven, passenger miles flown, number of cars through a toll, etc., as well as non-transit movement, including the reduction or increase in the number of people going to bars and/or restaurants, school attendance records, workplace absenteeism, etc. It will be appreciated that unemployment may also be a mobility factor. For example, people who have lost their jobs may not leave their home as much, therefore reducing overall mobility.

It will be appreciated that the Case Density, Case Density IDW, and Case Density Mobility may be essential in understanding the spread of a contagious viral disease. Contagious human-to-human viruses spread along human vectors. It will be appreciated that vectors may be living organisms that may transmit infectious diseases between humans or from animals to humans. See e.g., http://www.eho.int/tdr/diseases-topics/vectors/en/. As defined herein, the term "human vector" may be refer to any way that a human transmits a virus (or any other illness) to another human. It will be appreciated that illnesses, up to and including pandemic-level illnesses may be viral, bacterial, fungal, and/or potentially of any other suitable sources. As such, the density of the human population along with its mobility along all possible avenues of movement (e.g., public and/or private transportation) are essential factors in determining transmission risk. Embodiments disclosed herein include density and mobility factors to predict PPE needs to increase the ability to predict the degree of spread and the locations to which the underlying disease may spread, and to increase the ability to predict other potential outcomes of the pandemic response system that may aid pandemic response efforts.

Mortality Risk Index may be used to identify the regions with the highest risk of critical illness and death due to the virus at the country, state, county, ZIP Code, Census tract, and/or health system levels, etc. It will be appreciated that the prediction of the mortality risk of diseases includes the Case Fatality Rate which measures the number of deaths divided by the number of cases of the disease. However, the Case Fatality Rate may be retrospective in nature and may not take into account potential changes in the diseases, the diseases' current and changing virility, the health or health risks of the population, nor the ability for humans to adapt to the disease. Embodiments disclosed herein take into account the health indicators of the underlying population, including the social, environmental, economic, behavioural factors and/or data, assess the risk factors to the contagious virus as well as the immune system's ability (or inability) to adapt, which allows for a more precise and truly predictive Mortality Risk Index for the disease. Additionally, the Mortality Risk Index may provide far greater visibility into the need for and types of medical interventions and countermeasures required to combat the virus and treat the affected. The Mortality Risk Index may be determined as the sum of (A) and (B):

$$\frac{\Sigma \ (\text{Mortality rate in each age bracket} * \% \text{ population in the age bracket})}{\Sigma \ (\text{Mortality rate in all age brackets}) + \Sigma \ (\text{Mortality rate of each comorbidity})} \quad (A)$$

$$\frac{\Sigma \ (\text{Mortality rate in each age comorbidity} * \% \text{ population with that comorbidity})}{\Sigma \ (\text{Mortality rate in all age brackets}) + \Sigma \ (\text{Mortality rate of each comorbidity})} \quad (B)$$

Comorbidities may include the underlying health conditions that increase susceptibility and/or risk to the specific disease. As defined herein, the term "comorbidities" may refer to when an individual has two or more disease that may lead to morbidity at the same time. For example, in the MRI, comorbidities may be when a patient has one or more additional disease (e.g., heart disease, chronic obstructive pulmonary disease, etc.) that potentially aggravates their response to the virus. Comorbidities are based on research into the disease itself and can be updated as new insights into the disease are discovered. Without considering the underlying health posture at the population level, mortality rate or case fatality rate information may be just a percentage, or a mathematical number, without offering values in treating an actual individual, human patient. Embodiments disclosed herein may increase the insights to clinicians in treating current patients and anticipating future healthcare delivery needs throughout the lifecycle of the pandemic.

FIG. 11 illustrates a work flow 1101 of predicting a Mortality Risk Index, according to at least one example embodiment described herein. As shown in FIG. 11, Blocks 1150, 1020, 1140, and 1090 represent inputs to the workflow; Block 1160 represents outputs of the work flow; and Blocks 1130, 1100, 1120, and 1170 represent users of the output of the work flow. It will be appreciated that the input Blocks 1150, 1020, 1140, and 1090 may be e.g., data sources 110a . . . n of FIG. 1; and the users Blocks 1130, 1100, 1120, and 1170 may be e.g., the users 140, 150 of FIG. 1.

In at least one example embodiment, Block 1150 (see also Block 1010 of FIG. 10) represents health data, including disease (e.g., COVID-19) comorbidities, etc. Block 1020 (see also FIG. 10) represents social data including population demographics, etc. Block 1140 (see also 1040 of FIG. 10) represents the boundaries of a geographical area (e.g., a county, an area covered by a zip code, etc.). Block 1090 (see also FIG. 10) represents the symbology. As defined herein, the term "symbology" may refer to a way data is represented on a map. For example, the use of colour to reflect the level of risk in FIGS. 3 and 4. It will be appreciated that the input Blocks 1150, 1020, 1140, and 1090 may serve as the input data sources (e.g., to obtain the mortality rate in each/all age brackets, to obtain the percentage of population in a specific age bracket, to obtain the mortality rate in each comorbidity, etc.) for predicting or estimating the Mortality Risk Index (Block 1160).

In at least one example embodiment, Block 1130 represents users of the Mortality Risk Index including Supply Chain and/or Production Management Systems, etc. to perform actions such as scheduling production of the necessary PPE based on the Mortality Risk Index; providing logistics, transportation, delivery requirements, etc. to meet PPE customer needs, etc. Block 1100 represents users of the Mortality Risk Index including Government to provide improved coordination on PPE needs between governments at all levels. Block 1120 represents users of the Mortality Risk Index including Emergency Operations Managers such as stockpile and Inventory Management Systems to perform actions such as comparing existing PPE stock with PPE needs to issue orders for the distribution of PPE from inventory to where they are needed and/or for the acquisition of new PPE to meet anticipated needs.

In at least one example embodiment, Block 1170 represents users of the Mortality Risk Index including Healthcare Systems such as Inventory Management Systems to perform actions such as comparing existing PPE stock with PPE needs to issue orders for the distribution of PPE from inventory to the medical facilities where they are needed and/or for the acquisition of new PPE to meet anticipated needs; and providing PPE overuse, cleaning, and re-use protocols. It will be appreciated that the users Blocks 1130, 1100, 1120, and 1170 may be users of the Mortality Risk Index via infectious disease response engine platform, desktop software, mobile application, browser (e.g., web browser, etc.), messaging, etc.

FIG. 12 illustrates a work flow 1200 of predicting a Transmission Risk Index, according to at least one example embodiment described herein. As shown in FIG. 12, Blocks 1040, 1210, 1030, 1220, 1240, and 1090 represent inputs to the workflow; Blocks 1050, 1070, 1230, and 1250 represent intermediate and final outputs of the work flow; and Blocks 1130, 1100, 1120, and 1170 represent users of the output of the work flow. It will be appreciated that the input Blocks 1040, 1210, 1030, 1220, 1240, and 1090 may be e.g., data sources 110a . . . n of FIG. 1; and the users Blocks 1130, 1100, 1120, and 1170 may be e.g., the users 140, 150 of FIG. 1.

In at least one example embodiment, Block 1210 (see also Block 1010 of FIG. 10) represents health data, including disease (e.g., COVID-19) case statistics, etc. Block 1030 (see also FIG. 10) represents social data including population density, etc. Block 1220 represents the Mobility factors as determined by e.g., adherence to social distancing regulations (e.g., 6-feet apart between individuals). Block 1240 represents mobility data such as highway/car, air, bus, and/or metro routes, etc. Each route data include all of the areas (e.g., ZIP Codes areas) that each individual route passes through. Block 1040 (see also FIG. 10) represents the size of the area of e.g., a county, an area covered by a zip code, etc. and the boundaries (Block 1140). Block 1140 represents the boundaries (e.g., with other area) of a geographical area (e.g., a county, an area covered by a zip code, etc.). Block 1090 (see also FIG. 10) represents the symbology. It will be appreciated that the input Blocks 1040, 1210, 1030, 1220, 1240, and 1090 may serve as the input data sources (e.g., to obtain the number of cases (patients infected) in an area, to obtain the population in the area, to obtain the route data, etc.) for predicting or estimating the intermediate and final outputs such as Case Density (Block 1050), the IDW Geographic Weighting (Block 1070), the Mobility (Block 1230), and the Transmission Risk Index (Block 1250).

In at least one example embodiment, Block 1130 represents users of the Transmission Risk Index including Supply Chain and/or Production Management Systems, etc. to perform actions such as scheduling production of the necessary PPE based on the Transmission Risk Index; providing logistics, transportation, delivery requirements, etc. to meet PPE customer needs, etc. Block 1100 represents users of the Transmission Risk Index including Government to provide improved coordination on PPE needs between governments at all levels. Block 1120 represents users of the Transmission Risk Index including Emergency Operations Managers such as stockpile and Inventory Management Systems to perform actions such as comparing existing PPE stock with PPE needs to issue orders for the distribution of PPE from inventory to where they are needed and/or for the acquisition of new PPE to meet anticipated needs.

In at least one example embodiment, Block 1170 represents users of the Transmission Risk Index including Healthcare Systems such as Inventory Management Systems to perform actions such as comparing existing PPE stock with PPE needs to issue orders for the distribution of PPE from inventory to the medical facilities where they are needed and/or for the acquisition of new PPE to meet anticipated needs; and providing PPE overuse, cleaning, and re-use protocols. It will be appreciated that the users Blocks 1130, 1100, 1120, and 1170 may be users of the Transmission Risk Index via infectious disease response engine platform, desktop software, mobile application, browser (e.g., web browser, etc.), messaging, etc.

FIG. 13 illustrates a work flow 1300 of predicting a Pandemic Risk Index, according to at least one example embodiment described herein. The work flow 1300 is a combination of work flow 1101 of FIG. 11 and work flow 1200 of FIG. 12. In work flow 1300, the Transmission Risk Index (Block 1250) and the Mortality Risk Index (Block 1160) are intermediate outputs to the Pandemic Risk Index (Block 1310). In at least one example embodiment, Block 1130 represents users of the Pandemic Risk Index including Supply Chain and/or Production Management Systems, etc. to perform actions such as scheduling production of the necessary PPE based on the Pandemic Risk Index; providing logistics, transportation, delivery requirements, etc. to meet PPE customer needs, etc. Block 1100 represents users of the Pandemic Risk Index including Government to provide improved coordination on PPE needs between governments at all levels. Block 1120 represents users of the Pandemic Risk Index including Emergency Operations Managers such as stockpile and Inventory Management Systems to perform actions such as comparing existing PPE stock with PPE needs to issue orders for the distribution of PPE from inventory to where they are needed and/or for the acquisition of new PPE to meet anticipated needs.

In at least one example embodiment, Block 1170 represents users of the Pandemic Risk Index including Healthcare Systems such as Inventory Management Systems to perform actions such as comparing existing PPE stock with PPE needs to issue orders for the distribution of PPE from inventory to the medical facilities where they are needed and/or for the acquisition of new PPE to meet anticipated needs; and providing PPE overuse, cleaning, and re-use protocols. It will be appreciated that the users Blocks 1130, 1100, 1120, and 1170 may be users of the Pandemic Risk Index via infectious disease response engine platform, desktop software, mobile application, browser (e.g., web browser, etc.), messaging, etc.

FIG. 14 illustrates a work flow of predicting PPE needs, according to at least one example embodiment described herein. As shown in FIG. 14, Blocks 1410, 1420, 1430, 1440, 1450, 1310, and 1090 represent inputs to the workflow; Blocks 1460 and 1470 represent intermediate and final outputs of the work flow; and Blocks 1482, 1484, 1486, 1490, 1492, 1494, 1496, 1498, 1402, 1404, 1406, and 1408 represent users of the output of the work flow. It will be appreciated that the input Blocks 1410, 1420, 1430, 1440, 1450, 1310, and 1090 may be e.g., data sources 110*a* . . . *n* of FIG. 1; and the users Blocks 1482, 1484, 1486, 1490, 1492, 1494, 1496, 1498, 1402, 1404, 1406, and 1408 may be e.g., the users 140, 150 of FIG. 1.

In at least one example embodiment, Block 1410 represents health data, including, disease (e.g., COVID-19) case statistics (Active Cases etc.) and hospitalizations statistics (hospitalization rate, hospitalization number, staffed beds, etc.) during a period of time, etc. Block 1420 represents health data, including disease (e.g., COVID-19) case statistics (Active Cases etc.) and ICU hospitalizations statistics (hospitalization rate, hospitalization number, staffed beds, etc.) during a period of time, etc. Block 1430 represents health data, including PPE Low and/or High Burn Rate by PPE type (e.g., non-surgical mask, surgical mask, gowns, groves, etc.) during a period of time (e.g., daily) for different types of workforces, etc. Block 1440 represents workforce data, including healthcare providers' data (numbers, work schedules, etc.), etc. Block 1450 represents workforce data, including first responders and/or police's data (numbers, work schedules, etc.), etc. It will be appreciated that it is critical to obtain or acquire the number of PPE users (e.g., 1440, 1450, etc.) to incorporate the users' inclinations and habits for PPE use. Block 1310 represents the Pandemic Risk Index determined in FIG. 13. Block 1090 (see also FIG. 10) represents the symbology. It will be appreciated that the input Blocks 1410, 1420, 1430, 1440, 1450, 1310, and 1090 may serve as the input data sources (e.g., to obtain the daily Low Burn Rate of each PPE type for each workforce, to obtain the daily High Burn Rate of each PPE type for each workforce, to obtain the work schedules and numbers of workforces, etc.) for predicting or estimating the intermediate and final outputs such as High PPE Rate and Low PPE Rate (Block 1460), and the Risk Based PPE Estimates (i.e., Index PPE Rate, Block 1470).

In at least one example embodiment, Block 1480 represents that the users Blocks 1482, 1484, 1486, 1490, 1492, 1494, 1496, 1498, 1402, 1404, 1406, and 1408 may be users of the Risk Based PPE Estimates via the infectious disease response engine platform, desktop software, mobile application, browser-based interface (e.g., web browser, etc.), SMS and/or other messaging systems, an API, JSON, standards-based Web Map Service (WMS), Web Feature Service (WFS), etc.

In at least one example embodiment, Block 1482 represents users (e.g., suppliers) of the Risk Based PPE Estimates including Supply Chain and/or Production Management Systems. Blocks 1482, 1484 (e.g., logistics), and 1486 (e.g., manufactures) may work with each other (see Block 1130 of FIG. 11) to perform actions such as placing orders of the necessary PPE and scheduling production of the necessary PPE based on the Risk Based PPE Estimates; providing logistics, transportation, delivery requirements, etc. to meet PPE customer needs, etc. Block 1490 represents users (e.g., Federal Government, Federal Emergency Management Agency, Department of Health and Human Services, stockpile managers, etc.) of the Risk Based PPE Estimates including Government to provide improved coordination on PPE needs between governments at all levels (e.g., Block 1492 State Government or State stockpile managers, etc., Block 1494 Local Governments, etc.). See Block 1100 of FIG. 11. Block 1496 represents users (e.g., Federal Emergency Operations Managers, etc.) of the Risk Based PPE Estimates including Emergency Operations Managers such as stockpile and Inventory Management Systems to perform actions such as comparing existing PPE stock with PPE needs to issue orders for the distribution of PPE from inventory to where they are needed (e.g., Block 1498 State Emergency Operations Managers, etc., Block 1402 Local Emergency Medical Services, fire departments, police departments, responders, etc.) and/or for the acquisition of new PPE to meet anticipated needs. See Block 1120 of FIG. 11.

In at least one example embodiment, Block 1404 represents users of the Risk Based PPE Estimates including Healthcare Systems such as Inventory Management Systems to perform actions such as comparing existing PPE stock with PPE needs to issue orders for the distribution of PPE from inventory to the medical facilities where they are needed (e.g., Block 1406 Hospitals, etc., Block 1408 medical facilities, etc.) and/or for the acquisition of new PPE to meet anticipated needs; and providing PPE overuse, cleaning, and re-use protocols. See Block 1170 of FIG. 11. For example, when the existing PPE stock/inventory is more than the Risk Based PPE Estimates and the difference is more than a predetermined threshold, no action may be taken. When the existing PPE stock/inventory is more than the Risk Based PPE Estimates and the difference is equal to or less than a predetermined threshold, or the existing PPE stock/inventory is equal to or less than the Risk Based PPE Estimates, actions (ordering, manufacturing, procuring, delivering, distributing of the PPE to meet the anticipated needs, etc.) may be taken.

FIG. 15 illustrates a work flow 1500 of predicting ventilator needs, according to at least one example embodiment described herein. It will be appreciated that FIG. 15 is the same or similar to FIG. 14 but FIG. 15 illustrates a different example (ventilator needs) from of FIG. 14 (PPE needs). As shown in FIG. 15, Blocks 1420, 1510, 1520, 1530, 1310, and 1090 represent inputs to the workflow; Blocks 1540 and 1550 represent intermediate and final outputs of the work flow; and Blocks 1110, 1120, 1130, and 1170 represent users of the output of the work flow. It will be appreciated that the input Blocks 1420, 1510, 1520, 1530, 1310, and 1090 may be e.g., data sources $110a \ldots n$ of FIG. 1; and the users Blocks 1110, 1120, 1130, and 1170 may be e.g., the users 140, 150 of FIG. 1.

In at least one example embodiment, Block 1420 represents health data, including disease (e.g., COVID-19) case statistics (Active Cases etc.) and ICU hospitalizations statistics (hospitalization rate, hospitalization number, staffed beds, etc.) during a period of time, etc. Block 1510 represents health data, including the total functioning ventilator count, etc. Block 1520 represents health data, including the utilization of the ventilators (e.g., number, percentage, etc.), etc. Block 1530 represents geographic data, including medical facility (that having ventilators) locations, etc. Block 1310 represents the Pandemic Risk Index determined in FIG. 13. Block 1090 (see also FIG. 10) represents the symbology. It will be appreciated that the input Blocks 1420, 1510, 1520, 1530, 1310, and 1090 may serve as the input data sources (e.g., to obtain the number of functioning ventilators, to obtain the location of the ventilators, to obtain the ventilator usage information, etc.) for predicting or estimating the intermediate and final outputs such as Ventilator locations (Block 1540), and the Risk Based Ventilator Estimates (Block 1550).

In at least one example embodiment, Block 1130 represents users of the Risk Based Ventilator Estimates including Supply Chain and/or Production Management Systems, etc. to perform actions such as scheduling production of the necessary ventilators based on the Risk Based Ventilator Estimates; providing logistics, transportation, delivery requirements, etc. to meet ventilator customer needs, etc. Block 1100 represents users of the Risk Based Ventilator Estimates including Government to provide improved coordination on ventilator needs between governments at all levels. Block 1120 represents users of the Risk Based Ventilator Estimates including Emergency Operations Managers such as stockpile and Inventory Management Systems to perform actions such as comparing existing ventilator stock with ventilator needs or estimates to issue orders for the distribution of ventilators from inventory to where they are needed and/or for the acquisition of new ventilators to meet anticipated needs.

In at least one example embodiment, Block 1170 represents users of the Risk Based Ventilator Estimates including Healthcare Systems such as Inventory Management Systems to perform actions such as comparing existing ventilator stock with ventilator needs or estimates to issue orders for the distribution of ventilators from inventory to the medical facilities where they are needed and/or for the acquisition of new ventilators to meet anticipated needs; and providing ventilator overuse, cleaning, and re-use protocols. It will be appreciated that the users Blocks 1130, 1100, 1120, and 1170 may be users of the Risk Based Ventilator Estimates via infectious disease response engine platform, desktop software, mobile application, browser (e.g., web browser, etc.), messaging, etc.

It will be appreciated that there may be other ways to assess PPE needs, including a model producing an average of multiple PPE burn rate models and PPE daily use data gathered from users at the local level. The burn rate model created for hospitals, fire rescue/EMS, and long-term care facilities, may be based on a host of inputs such as CDC guidelines on PPE use per patient, survey of PPE usage from frontline professionals, subject expert recommendations, PPE use by fire rescue/EMS in emergency response per resident ratio, specific roles of frontline medical personnel and the status of patients disease. Such method largely predicts PPE needs over a limited period of time based on patient and frontline user variables, and as such may require accurate information on these variables on a continuous basis to predict PPE need reliably. Embodiments disclosed herein may make predictions based on the number of frontline personnel using census data, which may be less complex but more flexible to allow PPE needs to be predicted in a much broader context. In addition, with adjustment to the burn rate coefficient (e.g., the constant), embodiments disclosed herein may predict PPE needs for a wide range of frontline users in different settings down to a ZIP Code level. Another advantage of the embodiments disclosed herein is that the embodiments provide a range of PPE needs (Low, Index, High rate) which allows entities to make an informed as well as a risk-based decision when procuring their PPE supplies. Creating a method that accurately predicts PPE needs has proven increasingly essential given the pandemic.

Embodiments disclosed herein may provide a feasible way for entities to know how much PPE they need ahead of time. The flexibility of the embodiments disclosed herein not only allows the embodiments to be used broadly across healthcare organizations, public safety, and emergency response, but also guides government stockpile acquisitions and PPE production requirements for suppliers. Embodiments disclosed herein may enable making PPE needs prediction in the pre- and post-pandemic phases, providing viable solutions that ultimately prevent the re-occurrence of PPE shortages in the future especially during critical events such as a future pandemics, or a potential second wave when the disease (e.g., COVID-19) may coexist a seasonal flu outbreak.

Embodiments disclosed herein provide a means to leverage the response engine to determine where virus testing is insufficient and therefore needed, to develop a pandemic testing strategy, and therefore, develop a vaccine deployment strategy. For testing, by tracking the number of tests performed in an area, the number of people in the area, the test positivity rate, the transmission risk (TRI), the mortality risk (MRI), and by comparing the WHO guidelines on successful testing metrics designed to ensure the overall results describe the penetration of the illness within the population, it may be determined where too many, too few, or just the right number of tests have been performed. Where too few tests have been performed, the response engine may inform where more tests may be performed. For vaccine, the TRI and MRI, in combination, may reveal where and the order in which vaccine roll out should take place.

It will be appreciated that the response engine disclosed herein may represent an application of geospatial systems (e.g., a spatial data infrastructure) to address health-care challenges that has not previously existed. The response engine may form a health database that includes diverse data sets as well as a broadly comprehensive set of analytic tools. These analytic tools include e.g., Tableau, open source coding platforms such as R and Python, as well as integration with other pure-play data platforms, such as Snowflake. The response engine also supports and continuously pushes the bounds of advanced analytic capabilities through machine learning, AI, geospatial analytics, and natural language processing engine.

The response engine represents expanding set of curated and catalogued data sets for application in healthcare, which may include established collection of curated data sets to support pandemic early warning, response, and recovery efforts. The data may include a diverse collection from satellite and Earth Observation data, to environmental data, transit and transportation data, mobile device communication and location data, data on in-person events, airline, hotel, and travel industry data, as well as data on healthcare facilities, outcomes, procedures, transactions, and costs and/or social determinants of health such as population data, demographic data, employment, income, etc., and all data disclosed herein may be geocoded and loaded to the response engine. It will be appreciated that some of the data sets may be privately available, some publicly, and some are data sets that are created, for example, a data set identifying the location and resources of all health facilities in Africa.

It will be further appreciated that the response engine may communicate (disseminate) information out to numerous sources. The response engine may also inform all risk-based industries (e.g., financial services, logistics, travel, aerospace, tourism, insurance, etc.) on health-related impacts on broader markets. For example, the health risk data generated by the response engine may inform the tourism industry (hotels, airlines, tour operators, cruise lines, etc.) both the future locations of hot zones and the relative risks of outbreaks of tourist destinations. This information may be used by the industry to plan accordingly, and possibly shift travellers to safer destinations. For example, one specific possibility to communicate the risk data on tourist destinations is to output the analysis as a risk score and feed on a periodic basis (e.g., daily, weekly, real-time, etc.) into a booking engine of a travel website and integrate with their pricing formula to automatically discount (or otherwise recommend) low-risk tourist destinations. This information may also be used by the global public health industry to establish a global/local testing strategy as well as a vaccine deployment strategy.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Different features, variations and multiple different embodiments have been shown and described with various details. What has been described in this application at times in terms of specific embodiments is done for illustrative purposes only and without the intent to limit or suggest that what has been conceived is only one particular embodiment or specific embodiments. It is to be understood that this disclosure is not limited to any single specific embodiments or enumerated variations. Many modifications, variations and other embodiments will come to mind of those skilled in the art, and which are intended to be and are in fact covered by both this disclosure. It is indeed intended that the scope of this disclosure should be determined by a proper legal interpretation and construction of the disclosure, including equivalents, as understood by those of skill in the art relying upon the complete disclosure present at the time of filing.

The herein described subject matter sometimes illustrates different components contained within, or connected with, different other components. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A method of tracking a disease, comprising:
generating a predictive model, wherein the predictive model includes a plurality of analyzer channels to customize or fine tune the predictive model to the disease,
wherein the generating of the predictive model includes training the predictive model by iteratively adjusting a weight of one or more of the plurality of analyzer channels until the predictive model passes the training by:
acquiring data based on population data and condition data by extracting data from a plurality of data sources,
identifying a first subset of the population data based on at least one criterion in which the first subset includes patients who tested positive for the disease,
identifying a second subset of the population data that includes patients who have at least developed antibodies to the disease based on the first subset and the condition data,
determining a correlation between the first subset and the second subset, wherein the correlation includes identifying which individuals are in the first subset and in the second subset,
determining whether the correlation between the first subset and the second subset meets or exceeds a predetermined threshold,
wherein if the correlation does not meet or exceed the predetermined threshold, adjusting the weight for the one or more of the plurality of analyser channels by modifying, deleting, or adding the one or more of the plurality of analyser channels and feeding the predictive model, iteratively, to re-test the predictive model to customize or fine tune the predictive model to the disease, in which at least one of the plurality of analyser channels corresponds to an observable condition with respect to the disease that places a patient at a greater risk of being affected by the infectious disease, and repeating the identification of which of the individuals are in the first subset and in the second subset until the correlation meets or exceeds the predetermined threshold in accordance with the adjustment, wherein the one or more of the plurality of analyser channels is broken down into analyzer features to provide additional sensitivity in identifying the patient at the greater risk of being affected by the infectious disease, and when the correlation meets or exceeds the predetermined threshold, outputting the predictive model;

obtaining a set of resource data, using the predictive model to predict a number of active patients for the disease, a hospitalization rate for the disease, and a number of resources from the plurality of data sources;

determining a number of PPE users, a first burn rate, and a second burn rate for a type of PPE based on the predictive model of the disease and the set of resource data;

predicting a first PPE consumption rate for the type of PPE based on the number of PPE users, the first burn rate for the type of PPE, the hospitalization rate for the disease, the number of active patients for the disease, and the number of resources based on the predictive model of the disease;

predicting a second PPE consumption rate for the type of PPE based on the number of PPE users, the second burn rate for the type of PPE, the hospitalization rate for the disease, the number of active patients for the disease, and the number of resources based on the predictive model of the disease;

determining an index PPE rate based on a pandemic risk index, the first PPE consumption rate for the type of PPE, the second PPE consumption rate for the type of PPE, and the first burn rate;

geocoding the index PPE rate and loading the geocoded index PPE rate into a geospatial data analytic response engine;

displaying the geocoded index PPE on a spatial data infrastructure;

triggering a resource allocation and/or procurement based on the index PPE rate on the spatial data infrastructure; and adjusting the set of resource data based on the resource allocation and/or procurement.

2. The method according to claim 1, further comprising:
determining a transmission risk index;
determining a mortality risk index; and
determining the pandemic risk index based on the transmission risk index and the mortality risk index.

3. The method according to claim 2, wherein determining the transmission risk index includes:
determining a patient density for the disease;
determining a patient density inverse distance weight for the disease;
determining a patient density mobility for the disease; and
determining the transmission risk index based on the patient density, the patient density inverse distance weight, and the patient density mobility.

4. The method according to claim 3, wherein the patient density for the disease is a number of cases for the disease per a predetermined number of people in a predetermined area.

5. The method according to claim 4, wherein the number of cases is determined based on the number of active patients in the predetermined area and a percentage of daily increases of the number of active patients in a predetermined period of time.

6. The method according to claim 5, wherein the predetermined period of time is a week.

7. The method according to claim 3, wherein determining the patient density inverse distance weight for the disease includes:
determining a plurality of inverse distance weights for the patient density in a geographical area;
determining the patient density inverse distance weight for the disease based on the plurality of inverse distance weights and the patient density for the geographical area.

8. The method according to claim 7, wherein determining the plurality of inverse distance weights for the patient density in the geographical area includes:
determining a predetermined number of neighbours for the geographical area;
determining an inverse distance weight for each of the neighbours for the geographical area.

9. The method according to claim 8, wherein the predetermined number of neighbours is a constant and the geographical area is a county.

10. The method according to claim 8, wherein the predetermined number of neighbours is a constant and the geographical area is an area covered by a ZIP Code.

11. The method according to claim 3, wherein determining the patient density mobility for the disease includes:
determining a plurality of areas a route passes through;
determining the patient density for each of the plurality of areas;
determining mobility factors based on predetermined regulations;
determining the patient density mobility for the disease based on the mobility factors, and the patient density for each of the plurality of areas.

12. The method according to claim 11, wherein each of the plurality of areas is an area covered by a ZIP Code.

13. The method according to claim 11, wherein the predetermined regulations include a predetermined distance between persons.

14. The method according to claim 2, wherein determining the mortality risk index includes:
determining a mortality rate for a range of ages and a mortality rate for all ages;
determining a percentage in population for the range of ages;
determining a mortality rate for a comorbidity;
determining a percentage in population for the comorbidity; and
determining the mortality risk index based on the mortality rate for the range of ages, the percentage in population for the range of ages, the mortality rate for the comorbidity, the percentage in population for the comorbidity, and the mortality rate for all ages.

15. The method according to claim 1, further comprising:
obtaining a number of the type of PPE;
determining PPE needs based on the number of the type of PPE, the index PPE rate, the first PPE consumption rate, and the second PPE consumption rate;
procuring the type of PPE based on the determined PPE needs.

16. The method according to claim 1, further comprising:
obtaining a number of the type of PPE;
determining PPE needs based on the number of the type of PPE, the index PPE rate, the first PPE consumption rate, and the second PPE consumption rate;
allocating the type of PPE based on the determined PPE needs.

17. The method according to claim 1, further comprising:
obtaining a number of the type of PPE;
determining PPE needs based on the number of the type of PPE, the index PPE rate, the first PPE consumption rate, and the second PPE consumption rate;
supplying the type of PPE based on the determined PPE needs.

18. The method according to claim 1, further comprising:
obtaining a number of the type of PPE;
determining phases of a lifecycle of a pandemic for the disease;
for each phases, determining PPE needs based on the number of the type of PPE, the index PPE rate, the first PPE consumption rate, and the second PPE consumption rate.

19. The method according to claim 1, wherein the disease includes COVID-19.

20. A non-transitory computer-readable medium having computer-readable instructions that, if executed by a computing device, cause the computing device to perform operations comprising the method of claim 1.

* * * * *